US009318869B2

(12) United States Patent
Chuang et al.

(10) Patent No.: US 9,318,869 B2
(45) Date of Patent: *Apr. 19, 2016

(54) 193NM LASER AND INSPECTION SYSTEM

(71) Applicant: KLA-Tencor Corporation, Milpitas, CA (US)

(72) Inventors: Yung-Ho Chuang, Cupertino, CA (US); J. Joseph Armstrong, Fremont, CA (US); Vladimir Dribinski, Livermore, CA (US); Yujun Deng, San Jose, CA (US); John Fielden, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/586,646

(22) Filed: Dec. 30, 2014

(65) Prior Publication Data

US 2015/0155680 A1 Jun. 4, 2015

Related U.S. Application Data

(63) Continuation of application No. 14/158,615, filed on Jan. 17, 2014, now Pat. No. 8,929,406.

(60) Provisional application No. 61/756,209, filed on Jan. 24, 2013.

(51) Int. Cl.
*H01S 3/30* (2006.01)
*H01S 3/108* (2006.01)
(Continued)

(52) U.S. Cl.
CPC .............. *H01S 3/1083* (2013.01); *G01N 21/84* (2013.01); *G01N 21/9501* (2013.01);
(Continued)

(58) Field of Classification Search
CPC ..... H01S 3/0092; H01S 3/0078; H01S 3/067; H01S 3/0602
USPC ........................................ 372/5, 6, 21, 22, 41
See application file for complete search history.

(56) References Cited

U.S. PATENT DOCUMENTS 4,178,561 A 12/1979 Hon et al.
5,144,630 A 9/1992 Lin
(Continued)

FOREIGN PATENT DOCUMENTS

CN 101702490 5/2010
DE 102007004235 1/2008
(Continued)

OTHER PUBLICATIONS

Dianov et al. "Bi-doped fiber lasers: new type of high-power radiation sources", Conference on Lasers and Electro-Optics, May 6-11, 2007, 2 pages.
(Continued)

*Primary Examiner* — Kinam Park
(74) *Attorney, Agent, or Firm* — Bever, Hoffman & Harms, LLP

(57) ABSTRACT

A laser for generating an output wavelength of approximately 193.4 nm includes a fundamental laser, an optical parametric generator, a fourth harmonic generator, and a frequency mixing module. The optical parametric generator, which is coupled to the fundamental laser, can generate a down-converted signal. The fourth harmonic generator, which may be coupled to the optical parametric generator or the fundamental laser, can generate a fourth harmonic. The frequency mixing module, which is coupled to the optical parametric generator and the fourth harmonic generator, can generate a laser output at a frequency equal to a sum of the fourth harmonic and twice a frequency of the down-converted signal.

20 Claims, 19 Drawing Sheets

(51) Int. Cl.
*H01S 3/00* (2006.01)
*H01S 3/067* (2006.01)
*H01S 3/06* (2006.01)
*G01N 21/95* (2006.01)
*G01N 21/84* (2006.01)
*G01N 21/956* (2006.01)

(52) U.S. Cl.
CPC .......... *G01N 21/956* (2013.01); *H01S 3/0092* (2013.01); *H01S 3/0602* (2013.01); *H01S 3/067* (2013.01); *G01N 2021/95676* (2013.01); *H01S 3/0078* (2013.01)

(56) References Cited

U.S. PATENT DOCUMENTS

| | | | |
|---|---|---|---|
| 5,563,702 A | 10/1996 | Emery et al. | |
| 5,572,598 A | 11/1996 | Wihl et al. | |
| 5,742,626 A | 4/1998 | Mead et al. | |
| 5,760,899 A | 6/1998 | Eismann | |
| 5,825,562 A | 10/1998 | Lai et al. | |
| 5,999,310 A | 12/1999 | Shafer et al. | |
| 6,201,601 B1 | 3/2001 | Vaez-Iravani et al. | |
| 6,212,310 B1 | 4/2001 | Waarts et al. | |
| 6,249,371 B1 | 6/2001 | Masuda et al. | |
| 6,271,916 B1 | 8/2001 | Marxer et al. | |
| 6,373,869 B1 | 4/2002 | Jacob | |
| 6,498,801 B1 | 12/2002 | Dudelzak et al. | |
| 6,590,698 B1 | 7/2003 | Ohtsuki et al. | |
| 6,608,676 B1 | 8/2003 | Zhao et al. | |
| 6,816,520 B1 | 11/2004 | Tulloch et al. | |
| 6,859,335 B1 | 2/2005 | Lai et al. | |
| 6,888,855 B1 | 5/2005 | Kopf | |
| 7,098,992 B2 | 8/2006 | Ohtsuki et al. | |
| 7,136,402 B1 | 11/2006 | Ohtsuki | |
| 7,313,155 B1 | 12/2007 | Mu | |
| 7,339,961 B2 | 3/2008 | Tokuhisa et al. | |
| 7,352,457 B2 | 4/2008 | Kvamme et al. | |
| 7,463,657 B2 | 12/2008 | Spinelli et al. | |
| 7,471,705 B2 | 12/2008 | Gerstenberger et al. | |
| 7,525,649 B1 | 4/2009 | Leong et al. | |
| 7,528,943 B2 | 5/2009 | Brown et al. | |
| 7,593,437 B2 | 9/2009 | Staroudoumov et al. | |
| 7,593,440 B2 | 9/2009 | Spinelli et al. | |
| 7,609,309 B2 | 10/2009 | Brown et al. | |
| 7,623,557 B2 | 11/2009 | Tokuhisa et al. | |
| 7,627,007 B1 | 12/2009 | Armstrong et al. | |
| 7,643,529 B2 | 1/2010 | Brown et al. | |
| 7,715,459 B2 | 5/2010 | Brown et al. | |
| 7,813,406 B1 | 10/2010 | Nguyen et al. | |
| 7,822,092 B2 | 10/2010 | Ershov et al. | |
| 7,920,616 B2 | 4/2011 | Brown et al. | |
| 7,952,633 B2 | 5/2011 | Brown et al. | |
| 7,999,342 B2 | 8/2011 | Hsu et al. | |
| 8,208,505 B2 | 6/2012 | Dantus et al. | |
| 8,238,647 B2 | 8/2012 | Ben-Yishay et al. | |
| 8,298,335 B2 | 10/2012 | Armstrong | |
| 8,309,443 B2 | 11/2012 | Tanaka et al. | |
| 8,319,960 B2 | 11/2012 | Aiko et al. | |
| 8,391,660 B2 | 3/2013 | Islam | |
| 8,503,068 B2 | 8/2013 | Sakuma | |
| 8,755,417 B1 | 6/2014 | Dribinski | |
| 8,873,596 B2 | 10/2014 | Dribinski | |
| 8,929,406 B2 * | 1/2015 | Chuang et al. ............. 372/5 | |
| 2001/0000977 A1 | 5/2001 | Vaez-Iravani et al. | |
| 2002/0109110 A1 | 8/2002 | Some et al. | |
| 2002/0114553 A1 | 8/2002 | Meat et al. | |
| 2002/0191834 A1 | 12/2002 | Fishbaine | |
| 2003/0147128 A1 | 8/2003 | Shafer et al. | |
| 2003/0161374 A1 | 8/2003 | Lokai | |
| 2004/0080741 A1 | 4/2004 | Marxer et al. | |
| 2005/0041702 A1 | 2/2005 | Fermann et al. | |
| 2005/0110988 A1 | 5/2005 | Nishiyama et al. | |
| 2005/0111081 A1 | 5/2005 | Shafer et al. | |
| 2005/0128473 A1 | 6/2005 | Karpol et al. | |
| 2005/0157382 A1 | 7/2005 | Kafka et al. | |
| 2005/0254049 A1 | 11/2005 | Zhao et al. | |
| 2005/0254065 A1 | 11/2005 | Stokowski | |
| 2006/0038984 A9 | 2/2006 | Vaez-Iravani et al. | |
| 2006/0171656 A1 | 8/2006 | Adachi et al. | |
| 2006/0239535 A1 | 10/2006 | Takada | |
| 2006/0291862 A1 | 12/2006 | Kawai | |
| 2007/0002465 A1 | 1/2007 | Chuang et al. | |
| 2007/0103769 A1 | 5/2007 | Kuwabara | |
| 2007/0146693 A1 | 6/2007 | Brown et al. | |
| 2007/0211773 A1 | 9/2007 | Gerstenberger et al. | |
| 2007/0263680 A1 | 11/2007 | Starodoumov et al. | |
| 2007/0291810 A1 | 12/2007 | Luo et al. | |
| 2008/0182092 A1 | 7/2008 | Bondokov et al. | |
| 2008/0186476 A1 | 8/2008 | Kusunose | |
| 2008/0204737 A1 | 8/2008 | Ogawa | |
| 2009/0084989 A1 | 4/2009 | Imai | |
| 2009/0128912 A1 | 5/2009 | Okada | |
| 2009/0180176 A1 | 7/2009 | Armstrong et al. | |
| 2009/0185583 A1 | 7/2009 | Kuksenkov et al. | |
| 2009/0185588 A1 | 7/2009 | Munroe | |
| 2009/0296755 A1 | 12/2009 | Brown et al. | |
| 2010/0188655 A1 | 7/2010 | Brown et al. | |
| 2010/0301437 A1 | 12/2010 | Brown et al. | |
| 2011/0062127 A1 | 3/2011 | Gu et al. | |
| 2011/0073982 A1 | 3/2011 | Armstrong et al. | |
| 2011/0085149 A1 | 4/2011 | Nathan | |
| 2011/0134944 A1 | 6/2011 | Kaneda et al. | |
| 2011/0222565 A1 | 9/2011 | Horain et al. | |
| 2011/0228263 A1 | 9/2011 | Chuang et al. | |
| 2011/0279819 A1 | 11/2011 | Chuang et al. | |
| 2012/0033291 A1 | 2/2012 | Kneip | |
| 2012/0092657 A1 | 4/2012 | Shibata | |
| 2012/0113995 A1 | 5/2012 | Armstrong | |
| 2012/0120481 A1 | 5/2012 | Armstrong | |
| 2012/0137909 A1 | 6/2012 | Hawes et al. | |
| 2012/0314286 A1 | 12/2012 | Chuang et al. | |
| 2013/0016346 A1 | 1/2013 | Romanovsky et al. | |
| 2013/0021602 A1 | 1/2013 | Dribinski et al. | |
| 2013/0064259 A1 | 3/2013 | Wakabayashi et al. | |
| 2013/0077086 A1 | 3/2013 | Chuang et al. | |
| 2013/0088706 A1 | 4/2013 | Chuang et al. | |
| 2013/0176552 A1 | 7/2013 | Brown et al. | |
| 2013/0194445 A1 | 8/2013 | Brown et al. | |
| 2013/0264481 A1 | 10/2013 | Chern et al. | |
| 2013/0313440 A1 * | 11/2013 | Chuang et al. ............. 250/372 | |
| 2014/0071520 A1 | 3/2014 | Armstrong | |
| 2014/0111799 A1 | 4/2014 | Lei et al. | |
| 2014/0153596 A1 | 6/2014 | Chuang et al. | |
| 2014/0158864 A1 | 6/2014 | Brown et al. | |
| 2014/0204963 A1 * | 7/2014 | Chuang et al. ............. 372/5 | |
| 2014/0226140 A1 | 8/2014 | Chuang et al. | |
| 2014/0291493 A1 | 10/2014 | Chuang et al. | |
| 2014/0305367 A1 | 10/2014 | Chuang et al. | |
| 2915/0007765 | 1/2015 | Dribinski | |
| 2015/0177159 A1 | 6/2015 | Brown et al. | |
| 2015/0200216 A1 | 7/2015 | Muramatsu et al. | |
| 2015/0275393 A1 | 10/2015 | Bondokov et al. | |
| 2015/0294998 A1 | 10/2015 | Nihtianov | |

FOREIGN PATENT DOCUMENTS

| | | |
|---|---|---|
| EP | 0532927 | 3/1993 |
| EP | 1194804 B1 | 7/2003 |
| EP | 2013951 | 1/2009 |
| JP | 2002-258339 A | 9/2002 |
| JP | 2006-060162 A | 3/2006 |
| JP | 2007-86108 † | 4/2007 |
| JP | 2007-206452 A | 8/2007 |
| JP | 2009-145791 | 7/2009 |
| JP | 2010-54547 | 3/2010 |
| JP | 2010-256784 | 11/2010 |
| JP | 2011-23532 A | 2/2011 |
| JP | 2011-128330 A | 6/2011 |
| WO | 03/069263 | 8/2003 |
| WO | 2005/022705 A2 | 3/2005 |
| WO | 2009/082460 | 7/2009 |
| WO | 2010/037106 | 4/2010 |

(56) References Cited

FOREIGN PATENT DOCUMENTS

| WO | 2012/154468 | 11/2012 |
|---|---|---|
| WO | 2013/015940 A2 | 1/2013 |
| WO | 2014067754 A2 | 5/2014 |

OTHER PUBLICATIONS

Kalita et al. "Multi-watts narrow-linewidth all fiber Yb-doped laser operating at 1179 nm", Optics Express, 18 (6), pp. 5920-5925 (2010).
Kashiwagi et al. "Over 10W output linearly-polarized single-stage fiber laser oscillating above 1160 nm using Yb-doped polarization-maintaining solid photonic bandgap fiber", IEEE Journal of Quantum Electronics, 47 (8), pp. 1136-1141 (2011).
Mead et al. "Solid-state lasers for 193-nm photolithography", Proc. SPIE 3051, Optical Microlithography X, pp. 882-889 (Jul. 7, 1997).
Saikawa et al. "52 mJ narrow-bandwidth degenerated optical parametric system with a large-aperture periodically poled MgO:LiNbO3 device", Optics Letters, 31 (#21), 3149-3151 (2006).
Sakuma et al. "High power, narrowband, DUV laser source by frequency mixing in CLBO", Advanced High-Power Lasers and Applications, Nov. 2000, pp. 7-14, Ushio Inc.
Sakuma et al. "True CW 193.4-nm light generation based on frequency conversion of fiber amplifiers", Optics Express 19 (#16), 15020-15025 (2011).
Sasaki et al. "Progress in the growth of a CsLiB6O10 crystal and its application to ultraviolet light generation", Optical Materials, vol. 23, 343-351 (2003).
Shirakawa et al. "High-power Yb-doped photonic bandgap fiber amplifier at 1150-1200nm", Optics Express 17 (2), 447-454 (2009).
Ter-Mikirtychev et al. "Tunable LiF:F2-color center laser with an intracavity integrated-optic output coupler", Journal of Lightwave Technology, 14 (10), 2353-2355 (1996).
Yoo et al. "Excited state absorption measurement in bismuth-doped silicate fibers for use in 1160 nm fiber laser", 3rd EPS-QEOD Europhoton Conference, Paris, France, Aug. 31-Sep. 5, 2008, 1 page.
Zavartsev et al. "High efficient diode pumped mixed vanadate crystal Nd:Gd0.7Y0.3VO4 laser", International Conference on Lasers, Applications, and Technologies 2007: Advanced Lasers and Systems, Valentin A. Orlovich et al. ed., Proc. of SPIE vol. 6731, 67311P (2007), 5 pages.
International Search Report and Written Opinion dated Jul. 11, 2014 for PCT/US2014/030989, filed Mar. 18, 2014 in the name of KLA-Tencor Corporation.
International Search Report and Written Opinion dated May 20, 2014 for PCT/US2014/016198, filed Feb. 13, 2014 in the name of KLA-Tencor Corporation.
International Search Report and Written Opinion dated May 13, 2014 for PCT/US2014/012902, filed Jan. 24, 2014 in the name of KLA-Tencor Corporation.
KLA-Tencor Corporation, U.S. Appl. No. 14/248,045, filed Apr. 8, 2014 and entitled "Passivation of Nonlinear Optical Crystals".
KLA-Tencor Corporation, U.S. Appl. No. 62/059,368, filed Oct. 3, 2014 and entitled "183nm Laser and Inspection System".
KLA-Tencor Corpoation, U.S. Appl. No. 14/210,355 filed Mar. 13, 2014 and entitled "193nm Laser and an Inspection System Using a 193nm Laser".
Raoult, F. et al., "Efficient generation of narrow-bandwidth picosecond pulses by frequency doubling of femtosecond chirped pulses", Jul. 15, 1998 / ol. 23, No. 14 / Optics Letters, pp. 1117-1119.
KLA-Tencor Corporation; PCT International Search Report dated Dec. 29, 2015 for Application No. PCT/US2015/051538, 3 pages.
Huang, Qiyu et al., "Back-Side Illuminated Photogate CMOS Active Pixel Sensor Structure With Improved Short Wavelength Response", IEEE Sensors Journal, vol. 11, No. 9, Sep. 2011, 5 pages.
Itzler, Mark et al., "InP-based Geiger-mode avalanche photodiode arrays for three-dimensional imaging at 1.06 μm", Proceedings of SPIE, vol. 7320 (2000), 12 pages.
Niclass, Cristiano et al., "Design and Characterization of a CMOS 3-D Image Sensor on Single Photon Avalanche Diodes", IEEE Journal of Solid-State Circuits, vol. 40, No. 9, Sep. 2005, 8 pages.
Paetzel, Rainer et al., "Activation of Silicon Wafer by Excimer Laser" 18th IEEE Conf. Advanced Thermal processing of Semiconductors—RTP 2010, 5 pages.
Stevanovic, Nenad et al., "A CMOS Image Sensor for High-Speed Imaging", 2000 IEEE Int'l. Conference Solid-State Circuits, 3 pages.
Dulinski, Wojciech et al., "Tests of a backside illuminated monolithic CMOS pixel sensor in an HPD set-up" Nuclear Instruments and Methods in Physics Research A 546 (2005) 274-280, 7 pages.
Sarubbi, F et al, "Pure boron-doped photodiodes: a solution for radiation detection in EUV lithography", Proceedings of the 38th EP Solid-State Device Research Conf., Edinburgh Int'l. Conf. Centre. Endiburgh, Scotland, UK, Sep. 15-19, 2008, Piscataway, NJ: IEEE, US, pp. 278-281.

\* cited by examiner
† cited by third party

Figures 1A and 1B

| Fundamental laser type | Nd:Vandate, Nd:YAG, Yb-doped fiber | | Nd:YLF | | Nd:YLF | | Yb-doped fiber | |
|---|---|---|---|---|---|---|---|---|
| Harmonic | Fundamental (short) | Fundamental (long) | Fundamental (short) | Fundamental (long) | Fundamental (short) | Fundamental (long) | Fundamental (short) | Fundamental (long) |
| $\omega$ | 1064.0 | 1065.0 | 1052.0 | 1054.0 | 1046.0 | 1048.0 | 1029.0 | 1031.0 |
| $\omega_s$ | 1417.2 | 1413.7 | 1461.6 | 1453.9 | 1485.3 | 1477.3 | 1558.4 | 1549.3 |
| $2\omega$ | 532.0 | 532.5 | 526.0 | 527.0 | 523.0 | 524.0 | 514.5 | 515.5 |
| $4\omega$ | 266.0 | 266.3 | 263.0 | 263.5 | 261.5 | 262.0 | 257.3 | 257.8 |
| $4\omega + \omega_s$ | 224.0 | 224.1 | 222.9 | 223.1 | 222.4 | 222.5 | 220.8 | 221.0 |
| $4\omega + 2\omega_s$ | 193.4 | 193.4 | 193.4 | 193.4 | 193.4 | 193.4 | 193.4 | 193.4 |

Figure 1D

| Fundamental laser type | Nd:Vandate, Nd:YAG, Yb-doped fiber | | Nd:YLF | | Nd:YLF | | Yb-doped fiber | |
|---|---|---|---|---|---|---|---|---|
| Harmonic | Fundamental (short) | Fundamental (long) | Fundamental (short) | Fundamental (long) | Fundamental (short) | Fundamental (long) | Fundamental (short) | Fundamental (long) |
| ω | 1064.0 | 1065.0 | 1052.0 | 1054.0 | 1046.0 | 1048.0 | 1029.0 | 1031.0 |
| ωs | 850.7 | 849.7 | 862.5 | 860.5 | 868.6 | 866.5 | 886.8 | 884.6 |
| 2ω | 532.0 | 532.5 | 526.0 | 527.0 | 523.0 | 524.0 | 514.5 | 515.5 |
| 3ω | 354.7 | 355.0 | 350.7 | 351.3 | 348.7 | 349.3 | 343.0 | 343.7 |
| 3ω + ωs | 250.3 | 250.4 | 249.3 | 249.5 | 248.8 | 249.0 | 247.3 | 247.5 |
| 3ω + 2ωs | 193.4 | 193.4 | 193.4 | 193.4 | 193.4 | 193.4 | 193.4 | 193.4 |

# 193NM LASER AND INSPECTION SYSTEM

PRIORITY APPLICATION

This application is a continuation of U.S. patent application Ser. No. 14/158,615 entitled "193 NM LASER AND INSPECTION SYSTEM" filed Jan. 17, 2014 which claims priority of U.S. Provisional Patent Application 61/756,209, filed on Jan. 24, 2013 and incorporated by reference herein.

RELATED APPLICATION

The present application is related to U.S. patent application Ser. No. 13/797,939, entitled "Solid-State Laser and Inspection System Using 193 nm Laser", filed on Mar. 12, 2013 by Chuang et al. and incorporated by reference herein.

BACKGROUND OF THE DISCLOSURE

1. Field of the Disclosure

This disclosure relates to a laser and specifically to a solid state or fiber laser that generates radiation near 193 nm and is suitable for use in inspection of photomasks, reticles, and/or wafers. The laser may be pulsed (Q-switched or mode-locked) or CW (continuous wave).

2. Related Art

Excimer lasers for generating light at 193 nm are well known in the art. Unfortunately, such lasers are not well suited to inspection applications because of their low laser pulse repetition rates and their use of toxic and corrosive gases in their lasing medium, which leads to high cost of ownership.

Solid state and fiber lasers for generating light near 193 nm are also known. Exemplary lasers use two different fundamental wavelengths or the eighth harmonic of the fundamental, either of which requires lasers or materials that are expensive or are not in high volume production. Moreover, most of these lasers have very low power output and are limited to laser pulse repetition rates of a few MHz or less.

Therefore, a need arises for a laser and preferably to a solid state or fiber laser that generates radiation near 193 nm and is suitable for use in inspection of photomasks, reticles, and/or wafers. Notably, such inspections at high speeds often require minimum laser pulse repetition rates of multiple MHz (e.g. greater than 50 MHz in some cases).

SUMMARY OF THE DISCLOSURE

A laser for generating an output wavelength of approximately 193.4 nm is described. This laser includes a fundamental laser, an optical parametric generator, a fourth harmonic generator, and a frequency mixing module. The optical parametric generator, which is coupled to the fundamental laser, can generate a down-converted signal. The fourth harmonic generator, which is coupled to the optical parametric generator, can generate a fourth harmonic. The frequency mixing module, which is coupled to the optical parametric generator and the fourth harmonic generator, can generate a laser output of a frequency equal to a sum of the fourth harmonic and twice a frequency of the down-converted signal. Notably, the frequency mixing module comprises two non-linear crystals. In one embodiment, a first non-linear crystal is configured to generate a frequency equal to a sum of the fourth harmonic and the frequency of down-converted signal by type-II conversion, and a second non-linear crystal is configured to generate the frequency equal to the sum of the fourth harmonic and the twice the frequency of the down-converted signal by type-I conversion.

Another laser for generating an output wavelength of approximately 193.4 nm is described. This laser includes a fundamental laser, first and second frequency doubling modules, an optical parametric generator, and a frequency mixing module. The first frequency doubling module, which is coupled to the fundamental laser, can generate a second harmonic. The second frequency doubling module, which is coupled to the first frequency doubling module, can generate a fourth harmonic. The optical parametric generator, which is coupled to the first frequency doubling module or the fundamental laser, can generate a down-converted signal. The frequency mixing module, which is coupled to the optical parametric generator and the second frequency doubling module, can generate a laser output of a frequency equal to a sum of the fourth harmonic and twice a frequency of the down-converted signal. Notably, the frequency mixing module comprises two non-linear crystals. In one embodiment, a first non-linear crystal is configured to generate a frequency equal to a sum of the fourth harmonic and a frequency of the down-converted signal by type-I conversion, and a second non-linear crystal is configured to generate the frequency equal to the frequency of the sum of the fourth harmonic and the twice the down-converted signal by type-II conversion.

Yet another laser for generating an output wavelength of approximately 193.4 nm is described. This laser includes a fundamental laser, a frequency doubling module, a frequency combiner, an optical parametric generator, and a frequency mixing module. The frequency doubling module, which is coupled to the fundamental laser, can generate a second harmonic. The frequency combiner, which is coupled to the frequency doubling module, can generate a third harmonic. The optical parametric generator, which is coupled to the frequency doubling module or the frequency combiner, can generate a down-converted signal. The frequency mixing module, which is coupled to the optical parametric generator and the frequency combiner, can generate a laser output of a frequency equal to a sum of the third harmonic and twice a frequency of the down-converted signal.

These 193.4 nm lasers can be constructed using components that are readily available and are relatively inexpensive. For example, the fundamental laser used in the various described embodiments can generate a fundamental frequency of approximately 1064.3 nm, approximately 1053 nm, approximately 1047 nm, or approximately 1030 nm. These fundamental lasers are readily available at reasonable prices in various combinations of power and repetition rate. The fundamental laser can include a laser diode or a fiber laser.

The optical parametric generator, implemented as an optical parametric amplifier (OPA) or as an optical parametric oscillator (OPO), can include a periodically poled non-linear optical crystal. Exemplary periodically poled non-linear crystals can be formed from lithium niobate (LN), magnesium-oxide doped lithium niobate (Mg:LN), stoichiometric lithium tantalate (SLT), magnesium-oxide doped stoichiometric lithium tantalate (Mg:SLT), or potassium titanyl phosphate (KTP).

The down-converted signal generated by the optical parametric generator has a signal wavelength of one of approximately 1380 nm to 1612 nm, 1416 nm, 818 nm to 918 nm, and 846 nm to 856 nm.

The frequency mixing module can include a cesium lithium borate (CLBO) crystal, a beta barium borate (BBO) crystal, or a lithium triborate (LBO) crystal. In one exemplary mixing technique, the fourth harmonic at a wavelength of approximately 266 nm is mixed with the down-converted signal at approximately 1416 nm (infra-red light) to generate a wavelength of approximately 224 nm. The approximately 224 nm light is then recombined with the down-converted signal to generate a wavelength of approximately 193 nm. These two frequency mixing stages contribute to the overall high efficiency and stability of the 193 nm laser. In some preferred embodiments, these two frequency mixing stages can include CLBO crystals, which at a temperature near 100° C., can perform these two conversions with high efficiency (e.g. non-linear coefficients can be approximately 0.5 to 1 pm $V^{-1}$) and small walk-off angles. In one embodiment, type II mixing in CLBO can be used for the conversion stage that generates the approximately 224 nm wavelength followed by type-I mixing in CLBO to generate the approximately 193 nm wavelength. In another embodiment, type-I mixing in CLBO can be used for the conversion stage that generates the approximately 224 nm wavelength followed by type-II mixing in CLBO to generate the approximately 193 nm wavelength. In some embodiments, one or both of these two frequency mixing stages may be performed using a non-linear optical crystal other than CLBO, such as BBO (beta barium borate) or LBO (lithium triborate).

The improved lasers for generating an output wavelength of approximately 193.4 nm described herein can be continuous-wave lasers, Q-switched lasers, mode-locked lasers, or quasi-continuous-wave lasers. Compared to eighth harmonic lasers, these improved lasers are significantly less expensive, and have longer life and better cost of ownership. Moreover, compared with low repetition rate lasers, these improved lasers can significantly simplify the illumination optics of the associated inspection system.

BRIEF DESCRIPTION OF THE DRAWINGS

FIG. 1D shows a table of exemplary wavelength ranges for the improved 193 nm lasers shown in FIGS. 1A and 1B.

FIG. 1E shows a table of exemplary wavelength ranges for the improved 193 nm laser shown in FIG. 1C.

DETAILED DESCRIPTION OF THE DRAWINGS

Figure 1A:
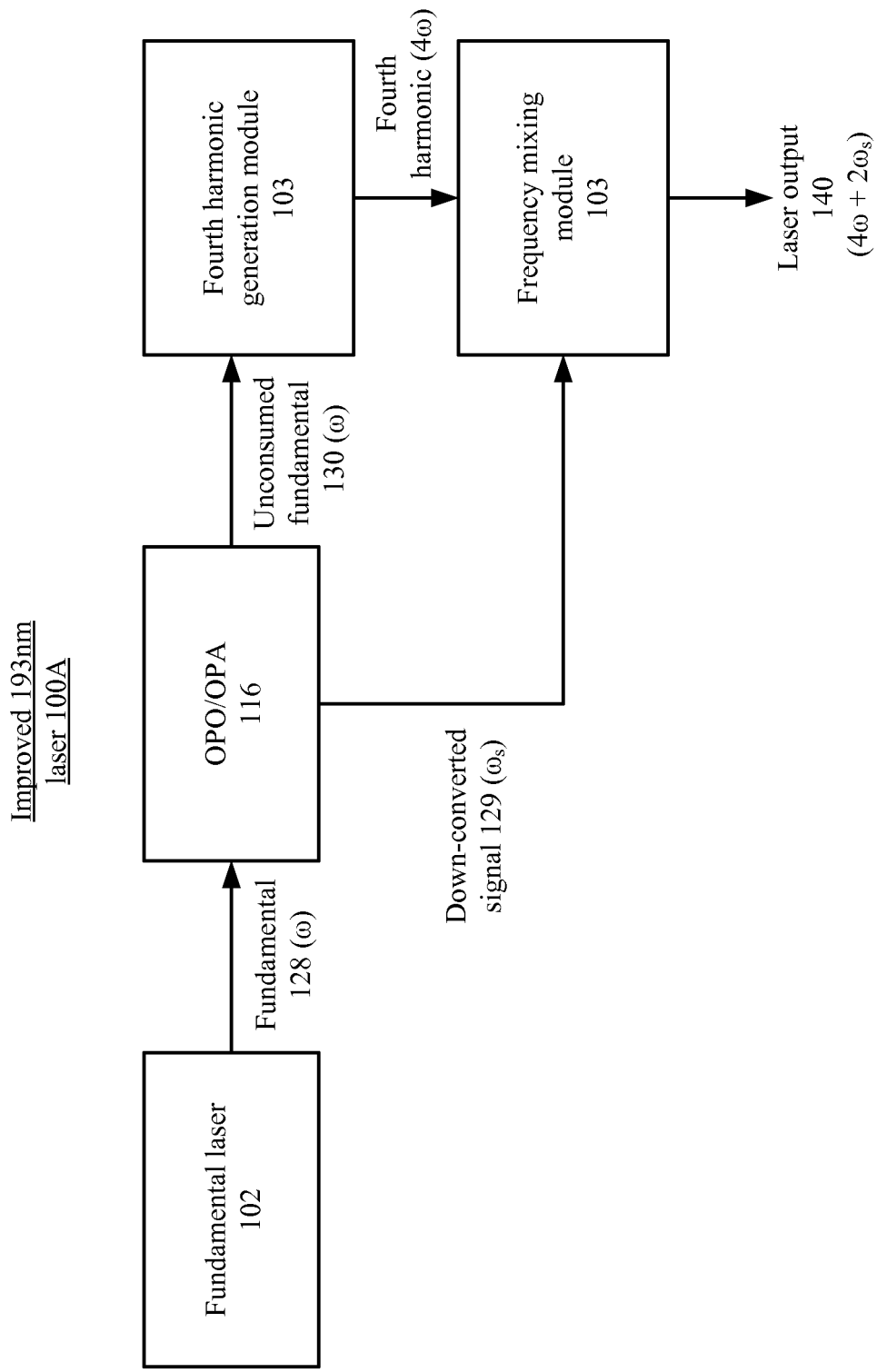
FIGS. 1A, 1B, and 1C show block diagrams of exemplary improved 193 nm lasers.

FIG. 1A shows a block diagram of an exemplary improved 193 nm laser 100A. In laser 100A, a fundamental laser 102 operating at a frequency ω can generate fundamental light 128 (called the "fundamental" in the industry). In one embodiment, the frequency ω (the fundamental) may correspond to an infra-red wavelength near 1064 nm. Note that when a wavelength is used herein without qualification, such wavelength refers to the vacuum wavelength of the light. An exemplary fundamental laser 102 can be implemented by a laser using a Nd:YAG (neodymium-doped yttrium aluminum garnate) lasing medium or a Nd-doped yttrium orthovanadate lasing medium or by an ytterbium-doped fiber laser. Suitable fundamental lasers are commercially available as pulsed (Q-switched or mode-locked) or CW (continuous wave) from Coherent Inc. (including models in the Paladin family with repetition rates of 80 MHz and 120 MHz), Newport Corporation (including models in the Explorer family) and other manufacturers. Laser power levels for such fundamental lasers can range from milliWatts to tens of Watts or more.

In laser 100A, the fundamental 128 is directed towards an optical parametric generator, e.g. an optical parametric oscillator or an optical parametric amplifier (OPO/OPA) 116. OPO/OPA 116 can down-convert part of the fundamental light 128 to a down-converted signal 129 of frequency $\omega_s$. In some preferred embodiments, the wavelength corresponding to $\omega_s$ is approximately 1416 nm (e.g. within a range from about 1330 nm to about 1612 nm, within a range from about 1378 nm to 1461 nm, or within a range from about 1413 nm to about 1417 nm).

In some embodiments, only part of the fundamental 128 is consumed in the down-conversion process. In such embodiments, the unconsumed part of the fundamental light 128, i.e. the unconsumed fundamental 130, is directed to a fourth harmonic generation module 103. Module 103 (described in further detail below) typically includes multiple frequency conversion stages to generate the $4^{th}$ harmonic (4ω) from the unconsumed fundamental (ω). This $4^{th}$ harmonic (4ω) can be combined with the down-converted signal 129 in a frequency mixing module 118 to create a laser output 140 having a frequency substantially equal to the sum of 4ω and $2\omega_s$. In some embodiments, the output wavelength of the laser output 140 is substantially equal to 193.368 nm. In other embodiments, the output wavelength is between approximately 190 nm and 200 nm or between approximately 192 nm and 195 nm.

Figure 1B:
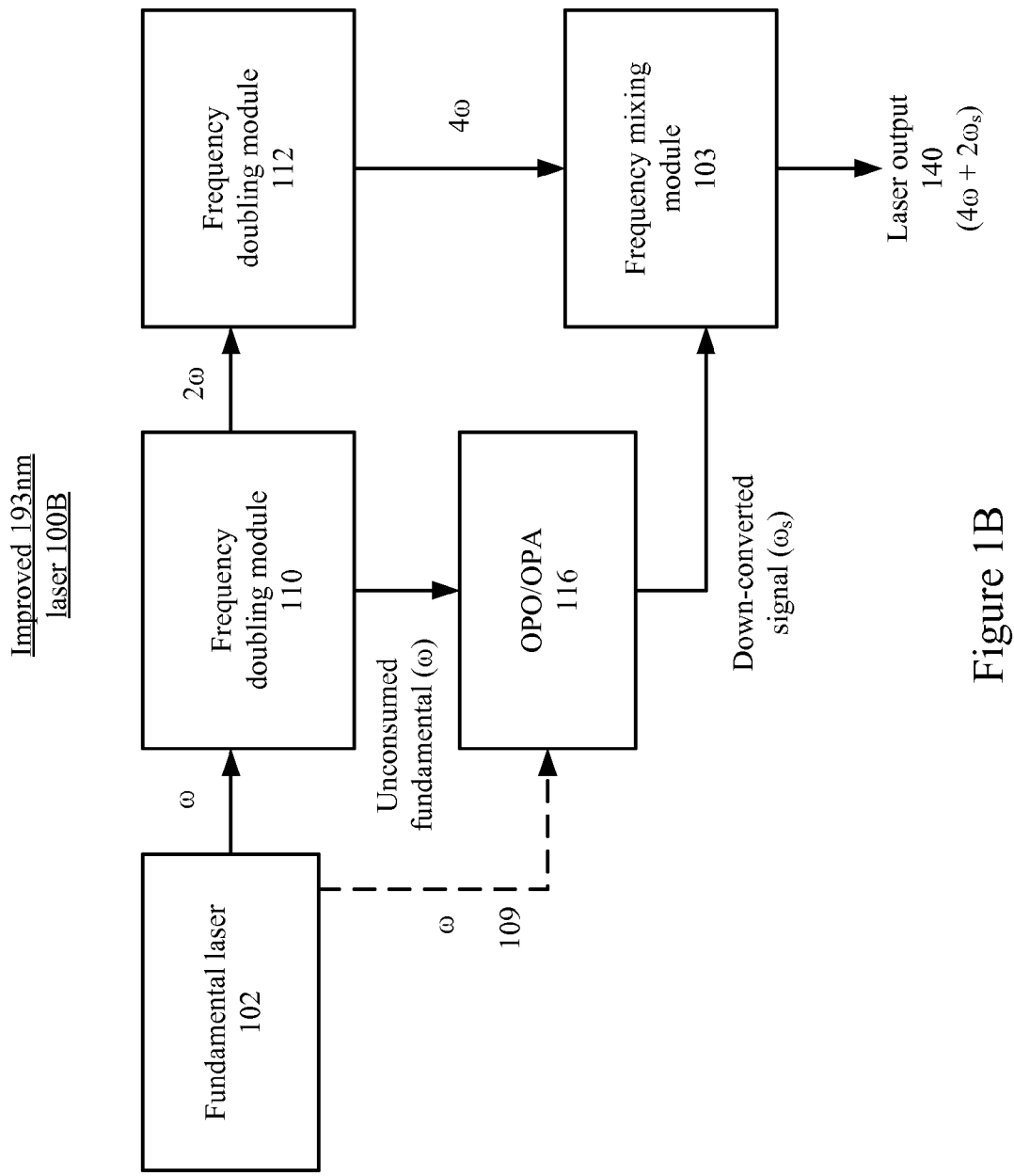

FIG. 1B shows a block diagram of an alternative improved 193 nm laser 100B. In this embodiment, the fundamental (ω) (generated by any of the above-mentioned lasers) is directed to a first frequency doubling module 110 to generate a second harmonic (2ω). The unconsumed fundamental output by the first frequency doubling module 110 can be directed to the OPO/OPA 116, which in turn generates the down-converted signal $\omega_s$. As noted above, the wavelength of the down-converted signal $\omega_s$ is approximately 1416 nm (e.g. within a range from about 1330 nm to about 1612 nm, within a range from about 1380 nm to 1461 nm, or within a range from about 1413 nm to about 1417 nm).

The second harmonic (2ω) generated by the first frequency doubling module 110 is directed to a second frequency doubling module 112 to generate a fourth harmonic (4ω). The frequency mixing module 103 can combine the fourth harmonic (4ω) and the down-converted signal ($\omega_s$) to create the laser output 140 having a frequency approximately equal to the sum of 4ω and 2$\omega_s$. As noted above, in some embodiments, this output wavelength is approximately equal to 193.368 nm. In other embodiments, the output wavelength is between approximately 190 nm and 200 nm or between approximately 192 nm and 195 nm.

In yet another embodiment, the fundamental (ω) output by the fundamental laser 102 can be split into two portions. One portion is directed to the first frequency doubling module 110, and the other portion is directed to the OPO/OPA 116 (shown by arrow 109). Thus, in this embodiment, the unconsumed fundamental ω output by the first frequency doubling module 110 is not directed to OPO/OPA 116. The second frequency doubling module 112 and the OPO/OPA 116 are both still coupled to the frequency mixing module 103, as shown in FIG. 1B. Substantially similar wavelengths are used and generated in this modified embodiment as in the above-described improved 193 nm laser 100B.

FIG. 1D shows a table of exemplary wavelength ranges (in nm) for the improved 193 nm lasers shown in FIGS. 1A and 1B. For each fundamental laser type, an exemplary short-wavelength fundamental and an exemplary long-wavelength fundamental are shown, along with the wavelengths corresponding to the harmonics and the down-converted signal required for the desired output wavelength (193.4 nm in the example shown in the table). The exact wavelength of a fundamental laser depends on many factors including the exact composition of the lasing medium, the operating temperature of the lasing medium, and the design of the optical cavity. Two lasers using the same laser line of a given lasing medium may operate at wavelengths that differ by a few tenths of 1 nm or a few nm due to the aforementioned and other factors. One skilled in the appropriate arts would understand how to choose the appropriate wavelength for the down-converted signal in order to generate the desired output wavelength from any fundamental wavelength close to those listed in the table. Similarly, if the desired output wavelength differs from 193.4 nm by a few nm, the desired output wavelength can also be achieved by an appropriate adjustment of the wavelength for the down-converted signal.

Figure 1C:
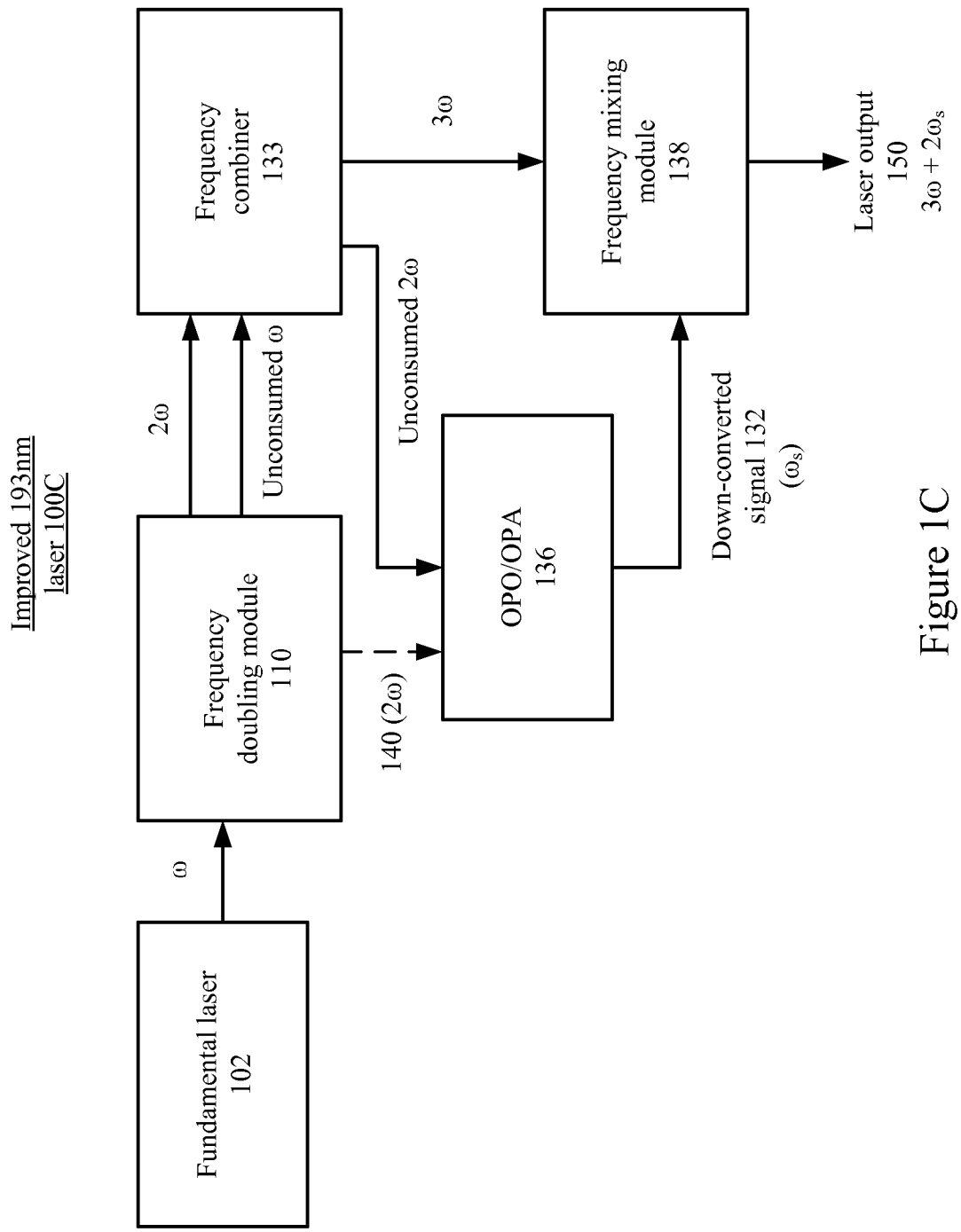

FIG. 1C shows another alternative embodiment of an improved 193 nm laser 100C. In this embodiment, the fundamental ω output by the fundamental laser 102 is directed to the frequency doubling module 110 to generate a second harmonic 2ω. The fundamental ω may be generated by any of the above-mentioned lasers. The portion of the fundamental ω not consumed in the frequency doubling module 110 and the second harmonic 2ω are then directed to a frequency combiner 133, which generates a third harmonic 3ω.

The second harmonic 2ω not consumed by the frequency combiner 133 is then directed to an OPO/OPA 136 to generate a down-converted signal 132 having a frequency $\omega_s$. In one modified embodiment (shown by arrow 140), a portion of the second harmonic 2ω can be taken directly from the output of the frequency doubling module 110 and directed to the OPO/OPA 136 (i.e. instead of taking the unconsumed second harmonic from the output of the frequency combiner 133). In some embodiments, the wavelength of the down-converted signal 132 is approximately 850 nm (e.g. within a range from about 818 nm to about 918 nm, or within a range from about 836 nm to 867 nm, or within a range from about 846 nm to about 856 nm). Note that the exact wavelength selected for $\omega_s$ depends on the exact wavelength of the fundamental laser and the desired output wavelength. Different fundamental lasers of the same type may differ in wavelength by a few tenths of a nm due to different lasing medium temperatures, lasing medium composition variations, and other small differences in the laser cavity design. In some embodiments, an output wavelength within a few nm of 193 nm is possible using the improved 193 nm laser, such as an output wavelength between 192 nm and 195 nm or between 190 nm and 200 nm.

A frequency mixing module 138 can combine the third harmonic 3ω and the down-converted signal 132 ($\omega_s$) to create a laser output 150 at a wavelength that corresponds to a frequency substantially equal to the sum of 3ω and 2$\omega_s$. In some embodiments, this output wavelength is substantially equal to 193.368 nm. In other embodiments, this output wavelength is between approximately 190 nm and 200 nm or between approximately 192 nm and 195 nm. In some embodiments, the frequency mixing module 138 may include a CLBO crystal to mix 3ω and $\omega_s$ to create the sum of these two frequencies at a wavelength of approximately 250 nm (when ω corresponds to a wavelength of approximately 1064 nm). In some embodiments, the frequency mixing module 138 may further include a BBO, KBBF (Potassium beryllium fluoroborate) or KBO (potassium pentaborate tetrahydride) crystal to mix the sum of 3ω+$\omega_s$ with $\omega_s$ to create the laser output 150 (corresponding to a wavelength of approximately 193.4 nm in one preferred embodiment). FIG. 1E shows a table of exemplary wavelength ranges (in nm) for the improved 193 nm laser shown in FIG. 1C. FIG. 1E shows analogous information to that shown in FIG. 1D for the improved 193 nm lasers of FIGS. 1A and 1B. See the detailed explanation above for FIG. 1D.

Figure 2:
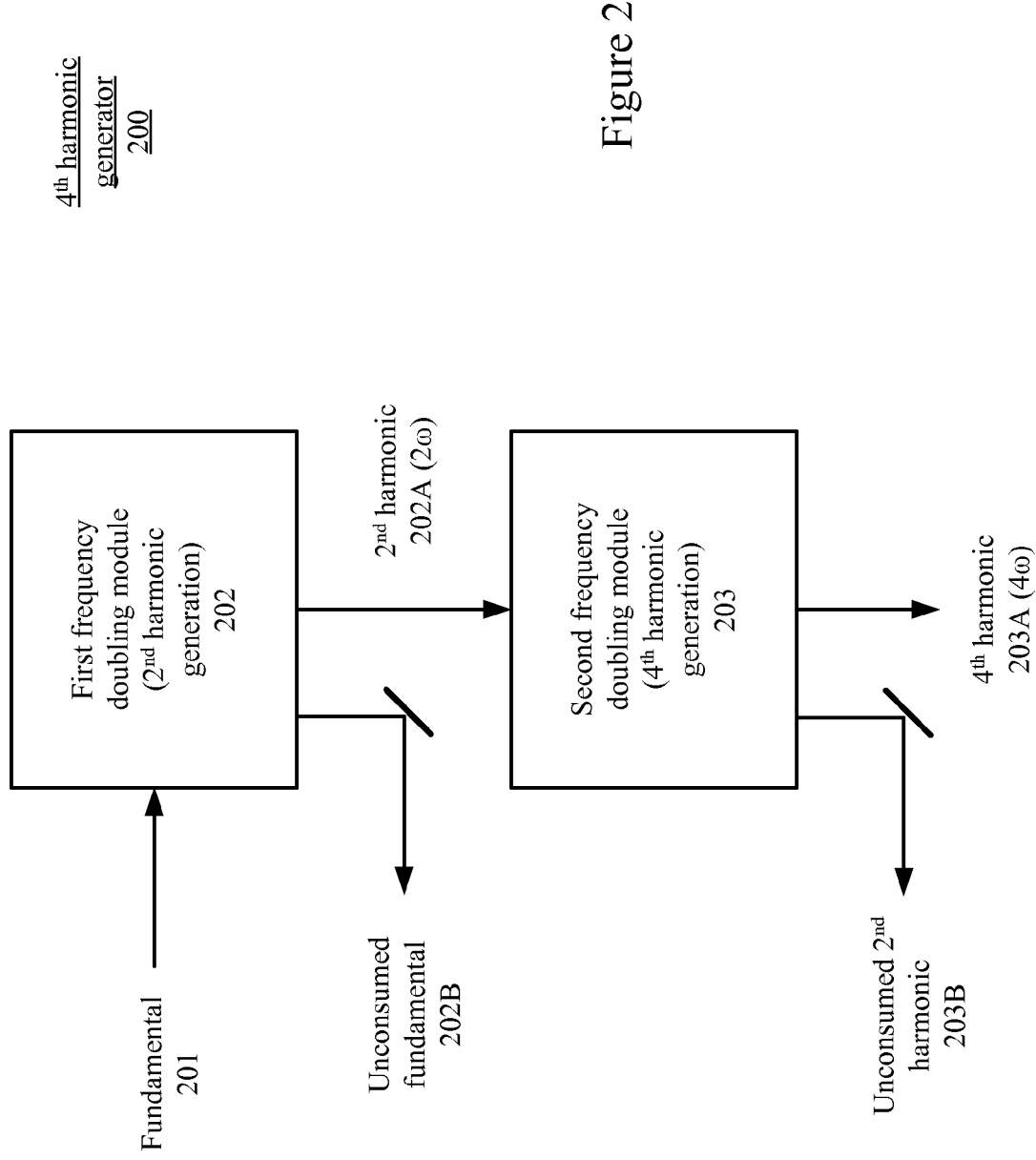
FIG. 2 shows one embodiment of a fourth harmonic generator.

FIG. 2 shows a preferred embodiment of a fourth harmonic generator 200. The fundamental 201 at frequency ω is converted to the second harmonic (2ω) 202A by a first frequency doubling module 202. The second harmonic 202A is converted to the fourth harmonic (4ω) 203A by a second frequency doubling module 203. The unconsumed fundamental 202B and the unconsumed second harmonic 203B not used within the first frequency doubling module 202 and the second frequency doubling module 203, respectively, may be output separately by these modules.

In one preferred embodiment of fourth harmonic generator 200, the second harmonic generation module 202 may comprise a LBO crystal for frequency conversion. In other embodiments, the second harmonic generation module 202 may comprise a CLBO, BBO, or other non-linear crystal for frequency conversion. In one preferred embodiment of fourth harmonic generator 200, the fourth harmonic generation module 203 may comprise a CLBO crystal for frequency conversion. In other embodiments, the fourth harmonic generation module 203 may comprise a BBO or other non-linear crystal for frequency conversion.

Figure 3:
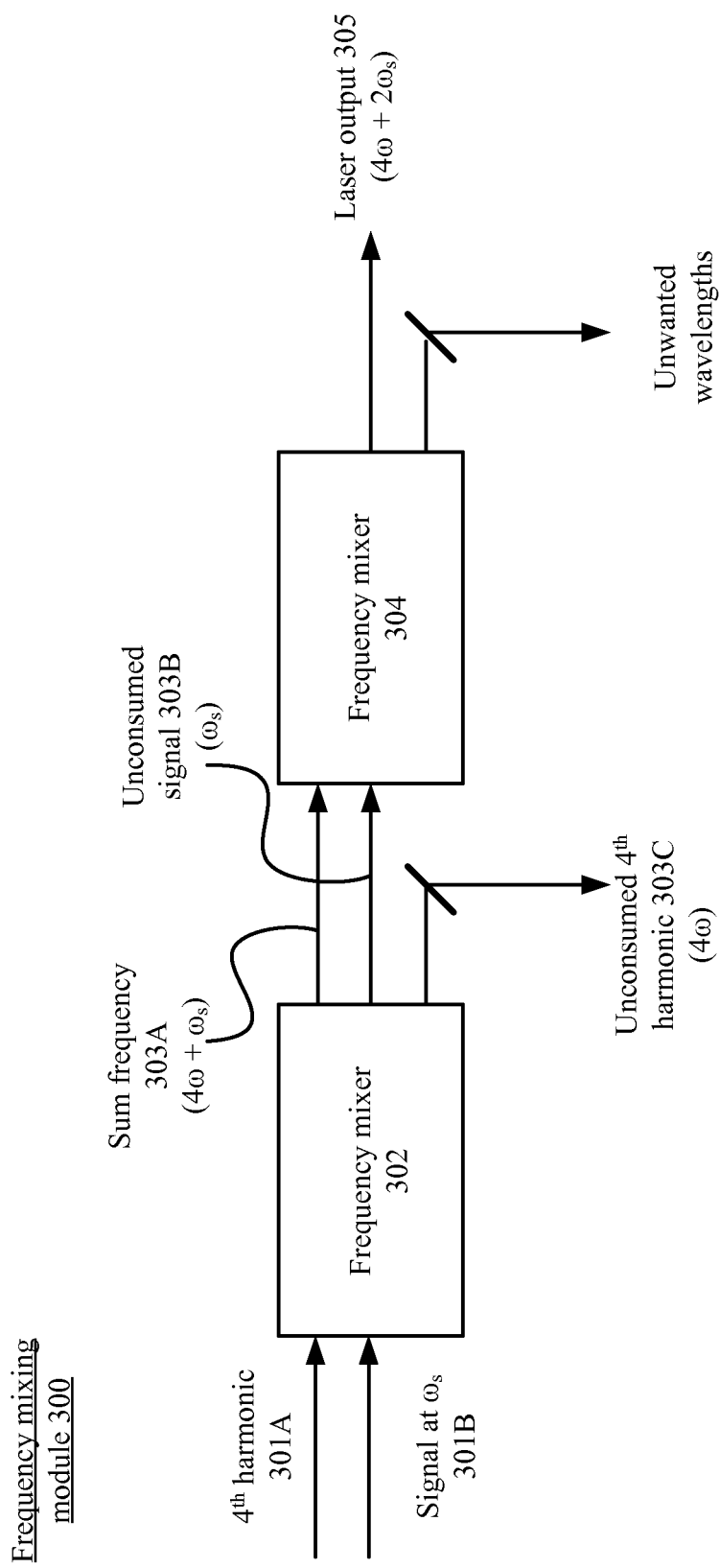
FIG. 3 shows one embodiment of a frequency mixer module.

FIG. 3 shows a preferred embodiment of a frequency mixer module 300. In frequency mixer module 300, a first frequency mixer 302 receives a fourth harmonic (4ω) 301A and a down-converted signal ($\omega_s$) 301B to generate a sum frequency 303A at a frequency equal to the sum of 4ω and $\omega_s$. The sum frequency 303A and an unconsumed signal 303B at frequency of $\omega_s$ are directed to a second frequency mixer 304, which generates a laser output 305 at a frequency of 4ω+2$\omega_s$. In some embodiments, the first frequency mixer 302 directs an unconsumed fourth harmonic 303C away from the second frequency mixer 304. In other embodiments, the unconsumed fourth harmonic 303C can be passed to the second frequency mixer 304 because, in those embodiments, the polarization of the second frequency mixer 304 is oriented such that it has little or no effect on the generation of the laser output 305.

In preferred embodiments, the sum frequency 303A is a frequency that is equivalent to a wavelength of approximately 224 nm. In some embodiments, the sum frequency 303A is substantially equal to the frequency corresponding to a wavelength of 223.95 nm. In other embodiments, the sum frequency 303A is a frequency corresponding to a wavelength in the range from approximately 221 nm to approximately 229 nm. In yet other embodiments, the sum frequency 303A is a frequency corresponding to a wavelength in the range from approximately 222 nm to approximately 226 nm. In preferred embodiments, frequency mixer 302 comprises a CLBO crystal for frequency conversion. In preferred embodiments, frequency mixer 304 comprises a CLBO crystal for frequency conversion.

Note that the frequency mixing module 138 (FIG. 1C) may be implemented in a similar manner to that illustrated in FIG. 3 for frequency mixing module 300, except that its inputs are the third harmonic (3ω) and the signal frequency ($\omega_s$) instead of the fourth harmonic (4ω) and the signal frequency ($\omega_s$). Some appropriate crystals for use in the frequency mixers 302 and 304 are described above. In particular, note that when frequency mixing module 300 is used for frequency mixing module 138, CLBO cannot be used in frequency mixer 304 for generating a wavelength near 193.4 nm because it does not phase match. As noted above, BBO, or another non-linear crystal, must be used in frequency mixer 304 in this case.

Note that in any of the embodiments shown in FIGS. 1A, 1B, 1C, 2, and 3, mirrors may be used to direct the fundamental or other wavelengths as needed. Prisms, beam splitters, beam combiners and dichroic coated mirrors, for example, may be used to separate and combine beams as necessary. Various combinations of mirrors and beam splitters may be used to separate and route the various wavelengths between different frequency generators and mixers in any appropriate sequence. The faces of frequency conversion crystals and prisms may be cut at an angle approximately or substantially equal to Brewster's angle for an incident wavelength in order to minimize or control reflection without using an anti-reflection coating. This cutting can be particularly advantageous for those surfaces where UV radiation is incident, since anti-reflection coatings may degrade when exposed to UV and thus may degrade the reliability of the laser if used on such surfaces. Waveplates or other optical elements may be used to rotate the polarization of any of the wavelengths as needed to align the polarization with the appropriate crystal axis of the next frequency conversion or frequency mixing stage.

FIGS. 1A, 1B, and 1C illustrate various improved lasers for generating a frequency substantially equal to four times the fundamental frequency (three times the fundamental frequency for FIG. 1C) plus two times the signal frequency, where the signal frequency is created by down-conversion from the fundamental (down-conversion from the second harmonic in FIG. 1C). Other laser embodiments similar to those described above for generating four times the fundamental frequency plus two times the signal frequency or three times the fundamental frequency plus two times the signal frequency are possible and are within the scope of this invention.

The above-described figures are not meant to represent the actual physical layout of the components. The above-described figures show the main optical modules involved in the process, but do not show every optical element. One skilled in the appropriate arts would understand how to build the improved laser from the above-described figures and their associated descriptions. It is to be understood that more or fewer mirrors or prisms may be used to direct the light where needed. Lenses and/or curved mirrors may be used to focus the beam waist to foci of substantially circular or elliptical cross sections inside or proximate to the non-linear crystals where appropriate. Prisms, gratings or diffractive optical elements may be used to steer or separate the different wavelengths at the outputs of each frequency convertor or mixer module when needed. Prisms, coated mirrors, or other elements may be used to combine the different wavelengths at the inputs to the frequency convertors and mixers as appropriate. Beam splitters or coated mirrors may be used as appropriate to divide one wavelength into two beams. Filters may be used to block undesired wavelengths at the output of any stage. Waveplates may be used to rotate the polarization as needed. Other optical elements may be used as appropriate. U.S. patent application Ser. No. 13/293,485, entitled "High Damage Threshold Frequency Conversion System", filed on May 17, 2012, and incorporated by reference herein, describes various optical elements particularly suited to use in the frequency conversion stages that generate UV wavelengths. In some cases, it may be acceptable to allow unconsumed light from one frequency conversion stage to pass to the next stage even though that light is not needed in the subsequent stage. This may be acceptable if the power density is low enough not to cause damage and if there is little interference with the desired frequency conversion process (for example because of no phase matching at the crystal angle or due to the polarization of the light). One skilled in the appropriate arts would understand the various tradeoffs and alternatives that are possible in the implementation of the improved laser.

In a preferred embodiment, the first frequency doubling module 110 (FIG. 1B) that generates the second harmonic can include a Lithium triborate (LBO) crystal, which is substantially non-critically phase-matched at temperature of about 149° C. to produce light at approximately 532 nm. In another embodiment, the second frequency doubling module 112 (FIG. 1B) that generates the fourth harmonic and the frequency mixers 302 and 304 (FIG. 3) can use critical phase matching in Cesium Lithium Borate (CLBO), beta-Barium Borate (BBO), LBO, or other non-linear crystals. In preferred embodiments, the second frequency mixer 304 includes a CLBO crystal that is critically phase matched with a high $D_{eff}$ (approximately 0.5 to 1 pm/V) and a low walk-off angle (less than about 35 mrad) at a temperature of approximately 100° C. This temperature is a convenient temperature to use because it minimizes absorption of water by the CLBO crystal. However, higher and lower temperatures may be used with appropriate adjustment of the angle of the crystal relative to the incident light. In some embodiments, the second frequency mixer 304 includes BBO, which has a larger walk-off angle (approximately 100 mrad) and a larger $D_{eff}$ (approximately 1 to 2 pm/V) compared with CLBO. In preferred embodiments, the frequency mixer 302 includes a CLBO crystal that is critically phase matched with a high $D_{eff}$ (approximately 0.8 pm/V) and a low walk-off angle (less than about 40 mrad) at a temperature of approximately 100° C. In that case, the second frequency mixer 304 can include BBO, which has a larger walk-off angle (approximately 96 mrad) and a larger $D_{eff}$ (approximately 1 to 2 pm/V) compared with CLBO.

The frequency doubling module 112 and the frequency mixers 302 and 304 may advantageously use some, or all, of the methods and systems disclosed in co-pending U.S. patent application Ser. No. 13/412,564, filed on Mar. 5, 2012 and entitled "Laser with high quality, stable output beam, and long-life high-conversion-efficiency non-linear crystal" by Dribinski et al. U.S. patent application Ser. No. 13/412,564 claims priority from U.S. Provisional Application No. 61/510,633, entitled "Mode-locked UV laser with high quality, stable output beam, long-life high conversion efficiency non-linear crystal and a wafer inspection system using a mode-locked laser", which was filed on Jul. 22, 2011. Both of these patent applications are incorporated by reference as if fully set forth herein.

Any of the harmonic generation stages (such as those performed by frequency doubling modules 110 and 112) and frequency mixing stages (such as performed by frequency mixers 302 and 304) may include one or more protective environments, such as those described in PCT Published Patent Application WO 2009/082460, entitled "Enclosure for controlling the environment of optical crystals", by J. Joseph Armstrong, and published on Jul. 2, 2009. This PCT publication is incorporated by reference as if fully set forth herein. Note that a single protective environment may enclose multiple stages or a single stage.

Further note that any of the harmonic generators (e.g. frequency doubling modules 110 and 112) may advantageously use hydrogen-annealed non-linear crystals. Such crystals may be processed as described in U.S. Provisional Application 61/544,425 filed on Oct. 7, 2011 by Chuang et al. and in co-pending U.S. patent application Ser. No. 13/488,635 filed on Jun. 1, 2012 by Chuang et al. These applications are incorporated by reference as if fully set forth herein. The hydrogen annealed crystals may be particularly useful in those stages involving deep UV wavelengths, including the frequency doublers 112 and 203 and the frequency mixers 302 and 304.

Figure 4A:
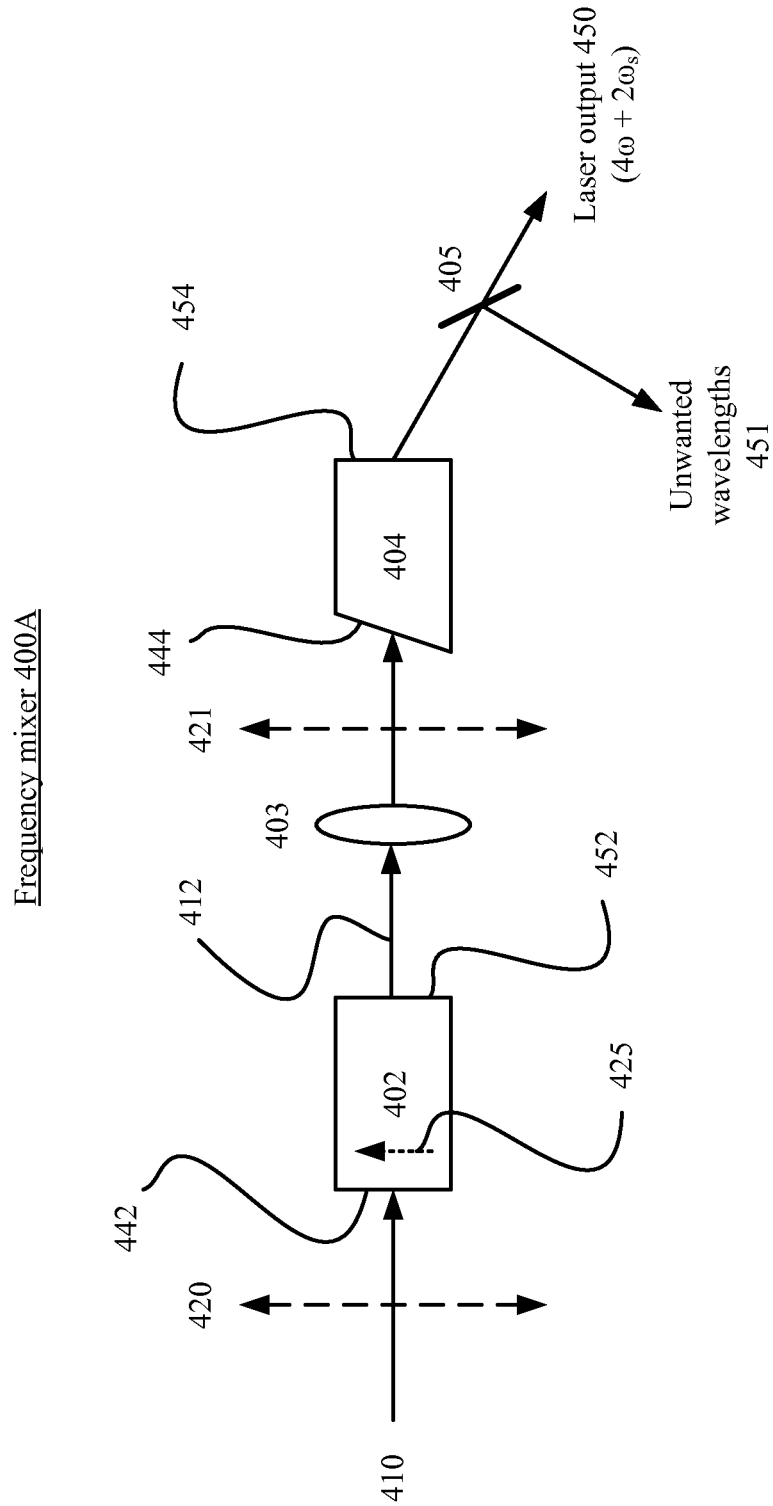
FIGS. 4A and 4B show some embodiments of frequency mixers that can be used in the improved 193 nm lasers.
Figure 4B:
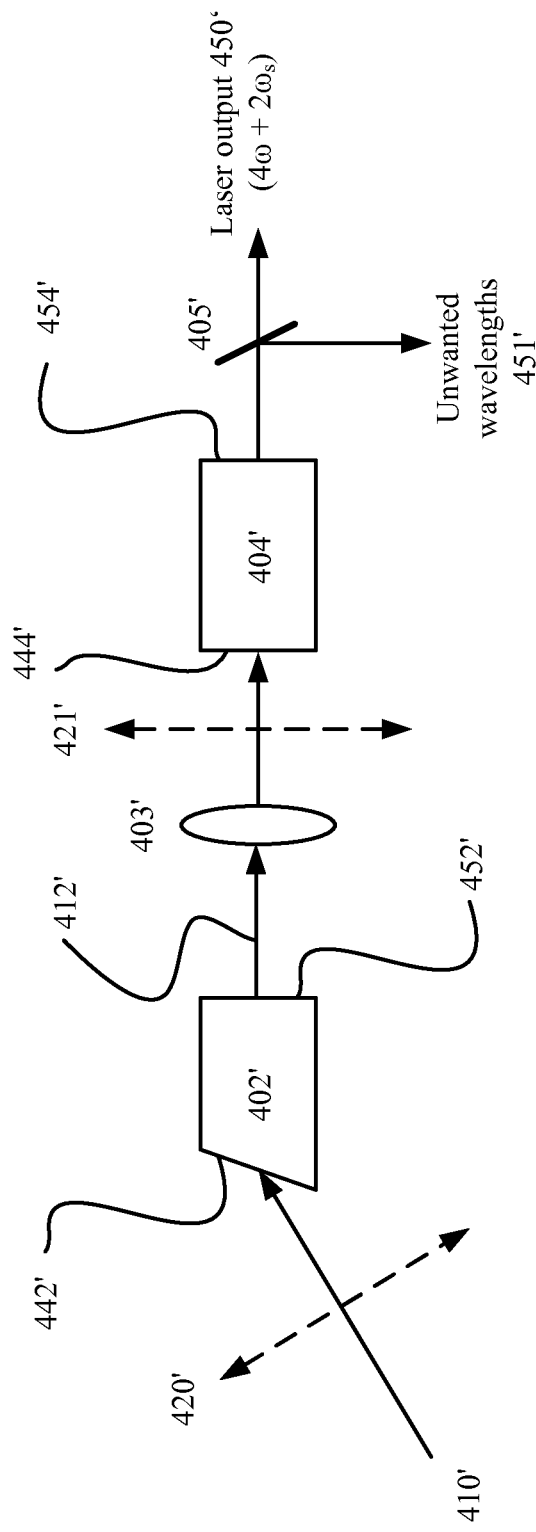

FIGS. 4A and 4B show some preferred embodiments of frequency mixers that can be used in the improved lasers described above. FIG. 4A illustrates one embodiment of a frequency mixer 400A in which type-II mixing is used for the first frequency mixing stage and type-I mixing is used for the final frequency mixing stage. Typically, three-wave mixing is done in a birefringent crystalline material (i.e. the refractive index depends on the polarization and direction of the light that passes through), where the polarizations of the fields and the orientation of the crystal are chosen such that the phase-matching condition is achieved. Typically, a birefringent crystal has three axes, one or two of which have a different refractive index than the other one(s). For example, uniaxial crystals have a single extraordinary (e) axis and two ordinary axes (o). If the two input frequencies have the same polarization (usually parallel to an o axis of the crystal), the phase matching is called "type-I phase-matching" and if their polarizations are perpendicular, it is called "type-II phase-matching". However, other conventions exist that specify further which frequency has what polarization relative to the crystal axis.

The first frequency mixing stage comprises a non-linear crystal 402, such as CLBO. The fourth harmonic and the signal wavelength enter the crystal 402 approximately collinearly in direction 410 and are focused to beam waists inside or proximate to this crystal (beam waists not shown). The signal wavelength is polarized with its electric-field vector in a direction shown by an arrow 420. The fourth harmonic is polarized substantially perpendicularly to the signal wavelength. The extraordinary (e) axis of the non-linear crystal 402 is oriented substantially parallel to the direction 420, as shown by an arrow 425. The plane containing the ordinary (o) axes of the non-linear crystal 402 are oriented substantially perpendicular to the direction 420. The o axes of the crystal 402 are rotated at an angle relative to the propagation direction of the light in the crystal so as to achieve phase matching. For type-II matching in CLBO at a temperature of approximately 100° C. with a signal wavelength near 1416 nm and a fourth harmonic wavelength near 266 nm, this angle is approximately 58.9°, and for BBO at approximately 100° C. with the same wavelengths, this angle is approximately 45.7°. One skilled in the appropriate arts understands how to choose different combinations of temperature and angle to achieve phase matching.

In some embodiments, the input surface 442 of crystal 402 is cut so as to be approximately at a Brewster's angle relative to the fourth harmonic (i.e. the direction 410). This angle minimizes reflection of the fourth harmonic wavelength without needing any anti-reflection coating on the input surface 442. In some embodiments, the input surface 442 may have an anti-reflection coating to reduce the reflected light at the fourth harmonic and/or the signal wavelengths. The output surface 452 of the crystal 402 may be coated or uncoated. The advantage of not coating is that coatings can have a short lifetime when exposed to intense UV radiation.

The output light 412 from crystal 402 is directed by optics 403 to the final frequency mixing stage, which includes a non-linear crystal 404. Note that three wavelengths exit crystal 402: the signal wavelength, the fourth harmonic wavelength, and a wavelength of the sum of the signal and the fourth harmonic. Because of the small walk-off angle, these three wavelengths are traveling approximately, but not exactly, collinearly. Optics 403 may include lenses, mirrors, prisms, beam splitters, and/or other optical elements. The optics 403 may refocus the beam waist inside, or proximate to, the crystal 404. In some embodiments, the optics 403 may approximately compensate for the walk-off so as to make the wavelengths more collinear as they enter crystal 404. In some embodiments, the optics 403 may separate out any unconsumed fourth harmonic. Other embodiments of the optics 403 may not separate the unconsumed fourth harmonic because it is polarized perpendicular to the polarization direction 421 and therefore will not be phase matched in the crystal 404. The polarization direction 421 is the direction of the electric field of both the signal wavelength and the wavelength of the sum of the signal and fourth harmonic wavelength. The polarization direction 421 is substantially parallel to the polarization direction 420 of the input signal wavelength. In some embodiments, the optics 403 may relatively delay by different amounts of time the pulses at different wavelengths so that they arrive substantially simultaneously inside the crystal 404. In other embodiments, the pulses are sufficiently long that the pulses overlap inside the crystal 404 without wavelength-dependent delays being incorporated into the optics 403. In some embodiments, the optics 403 may be omitted. The optics 403 may be omitted if the Rayleigh ranges of all the wavelengths are long enough that efficient mixing occurs in both crystals 402 and 403 without refocusing, provided also that the walk-off is small enough relative to the beam diameters, and the pulse lengths are long enough to have substantial overlap of the different wavelengths inside both crystals. The optics 403 may be coated or uncoated.

The crystal 404 may have its input surface 444 oriented at approximately a Brewster's angle for the wavelength corresponding to the sum of the signal and fourth harmonic. In such embodiments, the surface 444 can be uncoated, which has the advantage of reducing the susceptibility to damage by high intensity UV radiation. In other embodiments, the surface 444 may have an anti-reflection coating. In some embodiments, the surface 444 may be substantially perpendicular to the output light 412. The crystal 404 is oriented so that the plane containing its o axes is substantially parallel to the plane containing the polarization direction 421 and the direction of the output light 412 coming from the crystal 402. The e axis of crystal 404 is substantially perpendicular to the polarization direction 421. One o axis of the crystal 404 is rotated to an angle relative to direction of the output light 412 so as to achieve phase matching. For type I matching in CLBO at approximately 100° C. with wavelengths of approximately 1416 nm and 224 nm, this angle is approximately 65.4°. For BBO at approximately 100° C. for similar wavelengths, this angle is approximately 50.0°. In some embodiments, the output surface 454 is oriented at approximately a Brewster's angle relative to the laser output wavelength so as to maximize the transmission of the output wavelength. In the embodiment just described, the polarization direction of the output wavelength is perpendicular to the polarization direction 421.

Preferred embodiments may use optics 405 to separate the desired output wavelength, i.e. the laser output 450, from the other unwanted wavelengths 451. The optics 405 may include a beam splitter, a prism, a grating, or other optical elements. In some embodiments, the combination of walk-off and the angle of the output surface 454 of the crystal 404 may achieve sufficient separation of the laser output 450 from the other wavelengths that the optics 405 are not required.

FIG. 4B illustrates an alternative embodiment of a frequency mixer 400B in which type-I mixing is used for the first frequency mixing stage and type II-mixing is used for the final frequency mixing stage. The first frequency mixing stage includes a non-linear crystal 402', such as CLBO. The fourth harmonic (4ω) and the signal ($\omega_s$) wavelength enter the crystal 402' approximately collinearly along a direction 410' and are focused to beam waists inside or proximate to the crystal 402' (beam waists not shown). In this embodiment, both the signal wavelength and the fourth harmonic are polarized with their electric-field vectors substantially parallel to one another in the direction shown by the arrow 420'. The plane containing the o axes of the crystal 402' is parallel to the plane containing the directions 420' and the direction of propagation of the light in the crystal 402'. The e axis of the crystal 402' is perpendicular to the plane of the page of FIG. 4B. The o axes of the crystal 402' are rotated at an angle relative to the direction of the light propagating in the crystal 402' so as to achieve phase matching. For type I matching in CLBO at a temperature of approximately 100° C. with a signal wavelength near 1416 nm and a fourth harmonic wavelength near 266 nm, this angle is approximately 53.5°. For BBO at approximately 100° C. with similar wavelengths, this angle is approximately 42.4°. One skilled in the appropriate arts understands how to choose different combinations of temperature and angle to achieve phase matching.

In some embodiments, an input surface 442' of the crystal 402' is cut so as to be approximately at Brewster's angle relative to the direction 410' for the fourth harmonic wavelength. This angle minimizes reflection of the fourth harmonic wavelength without needing any anti-reflection coating on the input surface 442'. In some embodiments, the input surface 442' may have an anti-reflection coating to reduce the reflected light at the fourth harmonic and/or the signal wavelengths. An output surface 452' of the crystal 402' may be coated or uncoated. The advantage of not coating is that coatings can have a short lifetime when exposed to intense UV radiation.

An output light 412' from the crystal 402' is directed by optics 403' to the final frequency mixing stage including a non-linear crystal 404'. The optics 403' performs the same functions as the optics 403 described above in reference to FIG. 4A. The optics 403' may be implemented with similar elements to those described for the optics 403. Some embodiments of the frequency mixer 400B may omit the optics 403'.

A direction 421' is the direction of the electric field of both the signal and any unconsumed fourth harmonic. The direction 421' is substantially parallel to the direction 420' of the signal wavelength. The light at the wavelength corresponding to the sum of the signal and fourth harmonic is polarized perpendicularly to the direction 421'.

In the frequency mixer 400B, a crystal 404' may have its input surface 444' oriented at approximately Brewster's angle for the wavelength corresponding to the sum of the signal and fourth harmonic. In such embodiments, the surface 444' can be uncoated, which has the advantage of reducing the susceptibility to damage by high intensity UV radiation. In other embodiments, the surface 444' may have an anti-reflection coating. In some embodiments, the surface 444' may be substantially perpendicular to the light 412. The crystal 404' is oriented so that the plane containing its o axes is substantially perpendicular to the direction 421', and its e axis is substantially parallel to the direction 421'. The o axes of the crystal 404' are rotated by an angle relative to direction of propagation of the light inside the crystal 404' so as to achieve phase matching. For type-II matching in CLBO at approximately 100° C. with wavelengths of approximately 1416 nm and 224 nm, this angle is approximately 72.7°, and for BBO at approximately 100° C. for similar wavelengths, this angle is approximately 53.1°. In some embodiments, an output surface 454' of the crystal 404' is oriented at approximately Brewster's angle relative to the laser output wavelength so as to maximize the transmission of the output wavelength. In the frequency mixer 400B, the polarization direction of the laser output 450' is perpendicular to the direction 421'.

Some preferred embodiments of the frequency mixer 400B use optics 405' to separate laser output 450' from other unwanted wavelengths 451'. The optics 405' may include a beam splitter, a prism, a grating, or other optical elements. In some embodiments, the combination of walk-off and the angle of the output surface 454' of crystal 404' may achieve sufficient separation of the laser output 450' from the unwanted wavelengths 451' that the optics 405' are not required.

In preferred embodiments of the frequency mixers 400A and 400B, a substantial fraction, or almost all, of the input fourth harmonic is consumed in the crystal 402/402' due to the use of a high power at the signal wavelength. Some preferred embodiments use high enough power levels for the signal that a substantial fraction, or almost all, of the sum plus signal frequency created in the crystal 402/402' is consumed in the crystal 404/404'.

When CLBO crystals are used for the final two mixing stages (i.e. 402 and 404 in frequency mixer 400A, or 402' and 404' in frequency mixer 400B), the embodiment of FIG. 4A using type II mixing followed by type I mixing has the advantage of having approximately twice as large non-linear coefficient for the final mixing (approximately 1 pm/V compared with approximately 0.5 pm/V), whereas the non-linear coefficients are similar for the first mixing stage.

When BBO crystals are used for both first and final stages, the difference in efficiency between the embodiments of FIGS. 4A and 4B is small because type-I conversion is about approximately two times more efficient than type-II for both mixing stages.

Figure 5:
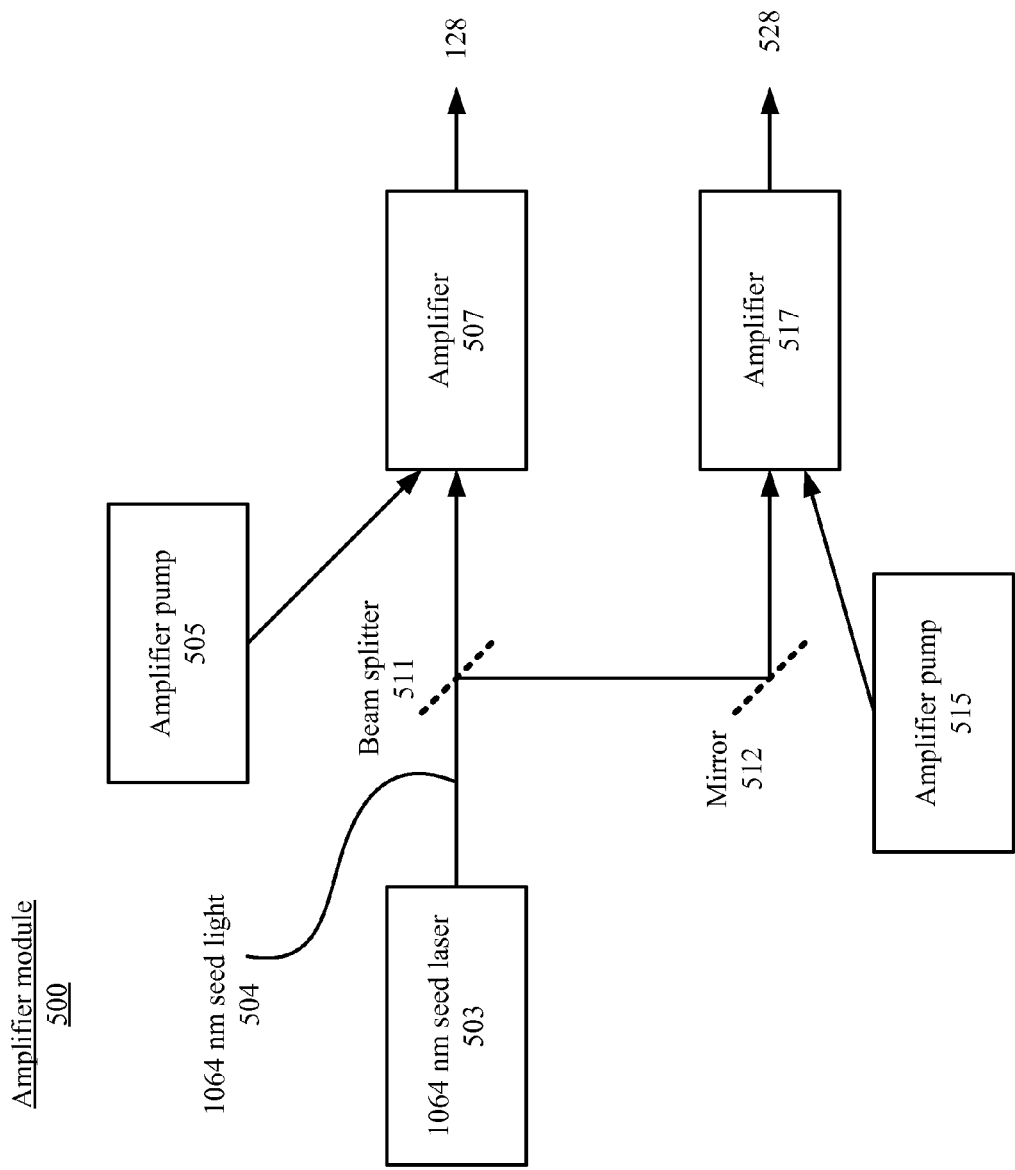
FIG. 5 illustrates an exemplary amplifier module in which a seed laser can generate stabilized, narrow-band seed laser light.

In some embodiments, in order to generate sufficient power at the fundamental wavelength of approximately 1064 nm, one or more amplifiers may be used to increase the power of the fundamental. If two or more amplifiers are used, then one seed laser should preferably be used to seed all the amplifiers so that they all output the same wavelength and the laser pulses are synchronized. FIG. 5 illustrates an exemplary amplifier module 500 in which a seed laser 503 can generate stabilized, narrow-band seed laser light 504 at the desired fundamental wavelength (e.g. approximately 1064 nm). In some embodiments, the seed laser 503 is one of a Nd doped YAG laser, a Nd-doped yttrium orthovanadate laser, a fiber laser, or a stabilized diode laser. The seed light 504 goes to a first amplifier 507 that amplifies the light to a higher power level. In some embodiments, the first amplifier 507 comprises Nd-doped YAG or Nd-doped yttrium orthovanadate. In one embodiment, an amplifier pump 505 includes a laser that can pump the first amplifier 507. In some embodiments, this pumping can be done using one or more diode lasers operating at approximately 808 nm in wavelength or at approximately 888 nm in wavelength. In other embodiments, the first amplifier 507 may comprise an Yb-doped fiber amplifier.

FIG. 5 also illustrates exemplary additional components that may be used in some embodiments of the amplifier module 500. Because the OPO/OPA 116, the frequency doubling module 110, and the frequency combiner 133 (FIGS. 1A, 1B, 1C) receive the fundamental laser wavelength as an input and depending on the output power required near 193.4 nm in wavelength, more fundamental laser light may be required that can be conveniently generated in a single amplifier at the required bandwidth, stability and beam quality. Indeed, increasing the power output of an optical amplifier can lead to increased bandwidth, degradation in the beam quality due to thermal lensing or other effects, reduced stability, and/or shortened lifetime.

Therefore, in some embodiments of the amplifier module 500, the first amplifier 507 and an additional second amplifier 517 can be used to respectively generate two fundamental laser outputs 128 and 528, which are directed to different frequency conversion stages. The second amplifier 517 can be substantially identical to the first amplifier 507. In one embodiment, an amplifier pump 515 includes a laser that can pump the second amplifier 517. The amplifier pump 515 can be substantially identical to the amplifier pump 505. Notably, the same seed laser 503 can be used to seed both lasers in order to ensure that the outputs 128 and 528 are at the same wavelength and are synchronized. A beam splitter 511 and a mirror 512 can divide the seed light 504 and direct a fraction of it to the second amplifier 517.

Figure 6:
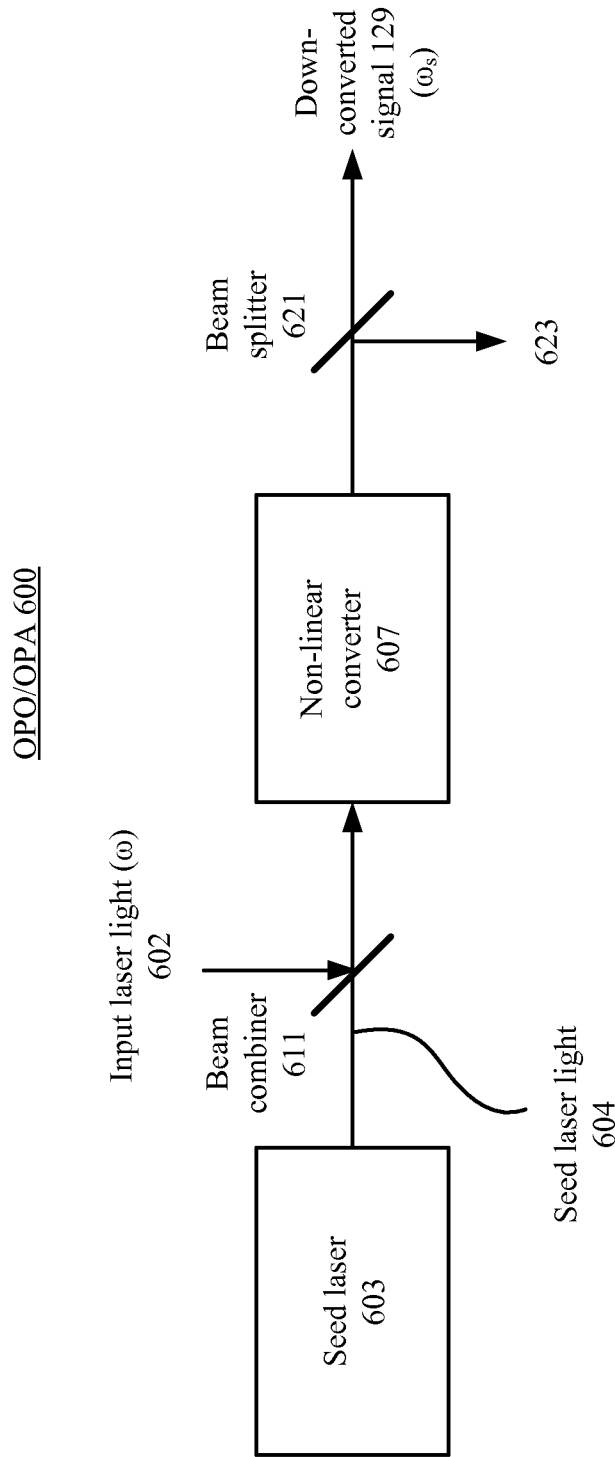
FIG. 6 illustrates an exemplary OPO/OPA configured to generate the down-converted signal at frequency $\omega_s$.

FIG. 6 illustrates an exemplary OPO/OPA 600 configured to generate the down-converted signal at frequency $\omega_s$. In this embodiment, a beam combiner 611 combines an input laser light 600 at the fundamental wavelength (the wavelength corresponding to the fundamental frequency $\omega$) and seed laser light 604 at a wavelength corresponding to the down-converted signal frequency $\omega_s$, which is generated by a seed laser 603.

The beam combiner 611 may comprise a dichroic coating that efficiently reflects a first wavelength while transmitting a second wavelength (for example, the beam combiner 611 may reflect the fundamental and transmit the seed laser light as shown, or vice-versa, not shown). After the beam combiner, the first and second wavelengths travel substantially collinearly through a non-linear converter 607, which may comprise periodically poled lithium niobate, magnesium oxide doped lithium niobate, KTP, or another suitable non-linear crystalline material.

In some preferred embodiments, the seed laser 603, such as a diode laser or a low-powered fiber laser, generates the seed laser light 604 having a wavelength of approximately 1416 nm (such as within a range from about 1330 nm to about 1612 nm, or within a range from about 1378 nm to 1461 nm, or within a range from about 1413 nm to about 1417 nm), which is then used to seed the down conversion process at the design frequency $\omega_s$. The seed laser 603 need only be of approximately 1 mW, a few mW, or a few tens of mW in power. In some preferred embodiments, the seed laser 603 is stabilized by using, for example, a grating and stabilizing the temperature. The seed laser 603 should preferably generate polarized light, which is then introduced into the non-linear converter 607 polarized substantially perpendicular to the polarization of the fundamental, i.e. the input laser light 602. In some embodiments, a non-linear crystal may be contained in a resonant cavity of the non-linear converter 607 to create a laser/amplifier based on spontaneous emission.

In this embodiment, a beam splitter 621 (or a prism in other embodiments) can separate the down-converted signal 129 at wavelength $\omega_s$ from an unconsumed fundamental 623. In other embodiments (not shown), the unconsumed fundamental 623 may be recirculated back to the input of the non-linear converter 607 with a time delay to match the next incoming laser pulse of the input laser light 602. Note that the OPO/OPA 136 (FIG. 1C) can be implemented in a similar configuration to that shown in FIG. 6 except that the input laser light 602 is at the second harmonic ($2\omega$), rather than the fundamental ($\omega$).

A quasi-CW laser may be constructed using a high repetition rate laser, such as a mode-locked laser operating at approximately 50 MHz or a higher repetition rate for the fundamental laser 102. A true CW laser may be constructed using a CW laser for the fundamental laser 102. A CW laser may need one or more of the frequency conversion stages to be contained in resonant cavities to build up sufficient power density to get efficient frequency conversion.

In one embodiment, a fundamental wavelength near 1030 nm is used instead of a fundamental of approximately 1064 nm. Such a wavelength can be generated by a laser using a gain medium of a Yb-doped YAG crystal or a Yb-doped fiber. With a 1030 nm fundamental wavelength, an OPO signal wavelength of approximately 1552.8 nm will generate a final output wavelength near 193.368 nm. A substantially similar frequency conversion scheme to the above can be used to generate the second harmonic (near 515 nm), the fourth harmonic (near 257.5 nm), the sum of the signal ($\omega_s$) and the fourth harmonic (near 220.9 nm), and the final output wavelength. BBO or CLBO may be used for the UV frequency conversion and mixing stages. Other non-linear crystals may also be suitable for some of the frequency conversion or mixing stages.

In yet another embodiment, a fundamental wavelength near 1047 nm or near 1053 nm is used instead of a fundamental of approximately 1064 nm. A laser operating near 1047 nm or near 1053 nm may be based on Nd:YLF (neodymium-doped yttrium lithium fluoride) for example. An appropriate signal wavelength can be chosen so as to achieve the desired laser output wavelength. For example, a signal frequency $\omega_s$ having a wavelength of approximately 1480 nm can generate a laser output of $4\omega+2\omega_s$ near 193.4 nm from a fundamental near 1047 nm. Alternatively, a signal frequency corresponding to a wavelength of approximately 1457 nm could be used with a fundamental near 1053 nm to generate a similar laser output.

In yet other embodiments, fundamental laser wavelengths near 1030 nm, 1047 nm, or 1053 nm can generate an output wavelength of approximately 193.4 nm using $3\omega+2\omega_s$, where $\omega_s$ is approximately 885 nm, 867 nm, or 861 nm, respectively.

The improved 193 nm laser is less complex and more efficient than, for example, 8th harmonic generation (which generally needs more frequency conversion stages), and much less complex than combining two different fundamental wavelengths. Therefore, the above-described improved 193 nm laser can provide significant system advantages during photomask, reticle, or wafer inspection.

The improved 193 nm laser has several advantages compared with the laser of U.S. patent application Ser. No. 13/797,939, filed by Chuang et al. on Mar. 12, 2013 (P3913). A first advantage is that the final frequency conversion stage of the improved 193 nm laser is more efficient at generating higher output power for a given fundamental power, or a lower power fundamental for the same output power. A second advantage is that optical components and test equipment operating near 1.4 µm or 1.5 µm are more readily available than near 2.1 µm in wavelength. A third advantage is that for a signal wavelength near 1.4 µm or 1.5 µm significantly more energy goes into the signal compared with the idler, thereby resulting in more efficient conversion of fundamental power to output power (compared with a signal wavelength near 2.1 µm where almost equal amounts of power must go into the signal and the idler). A fourth advantage is that a signal wavelength near 1.4 µm or near 1.5 µm is not close to any water or —OH absorption peak, therefore leading to greater tolerance of small amounts of moisture in any of the crystals or in the light path. A sixth advantage is that the final frequency mixing stage (e.g. frequency mixing module 103, FIG. 1A) uses only two input wavelengths (i.e. the fourth harmonic and the signal) instead of three input wavelengths (i.e. the fourth harmonic, the fundamental, and the signal). Note that many of the same advantages apply to the improved 193 nm laser (FIG. 1C) that combines the third harmonic with a signal wavelength between about 800 nm and 900 nm in wavelength.

Fundamental lasers operating near 1064 nm, 1053 nm, 1047 nm, and 1030 nm in wavelength are readily available at a range of different power levels and repetition rates including mode-locked, Q-switched, quasi-CW, and true CW lasers. The improved 193 nm laser is capable of operating at repetitions rates higher than 1 MHz, which is important for high-speed inspection applications. The use of mode-locked or quasi-CW fundamental laser operating at a repetition rate greater than 50 MHz, is particularly advantageous for high-speed inspection of semiconductor wafers, photomasks, and reticles because it allows high-speed image acquisition and reduces the peak power of each pulse (and so causes less damage to the optics and to the article being inspected) compared with a lower repetition rate laser of the same power. Although the above embodiments describe using various fundamental wavelengths to generate a laser output of 193.3 nm, other wavelengths within a few nanometers of 193.3 nm can be generated using an appropriate choice of signal wavelength. Such lasers and systems utilizing such lasers are within the scope of this invention.

FIGS. 7-14 illustrate systems that can include one of the above-described improved 193 nm lasers. These systems can be used in photomask, reticle, or wafer inspection and metrology applications.

Figure 7:
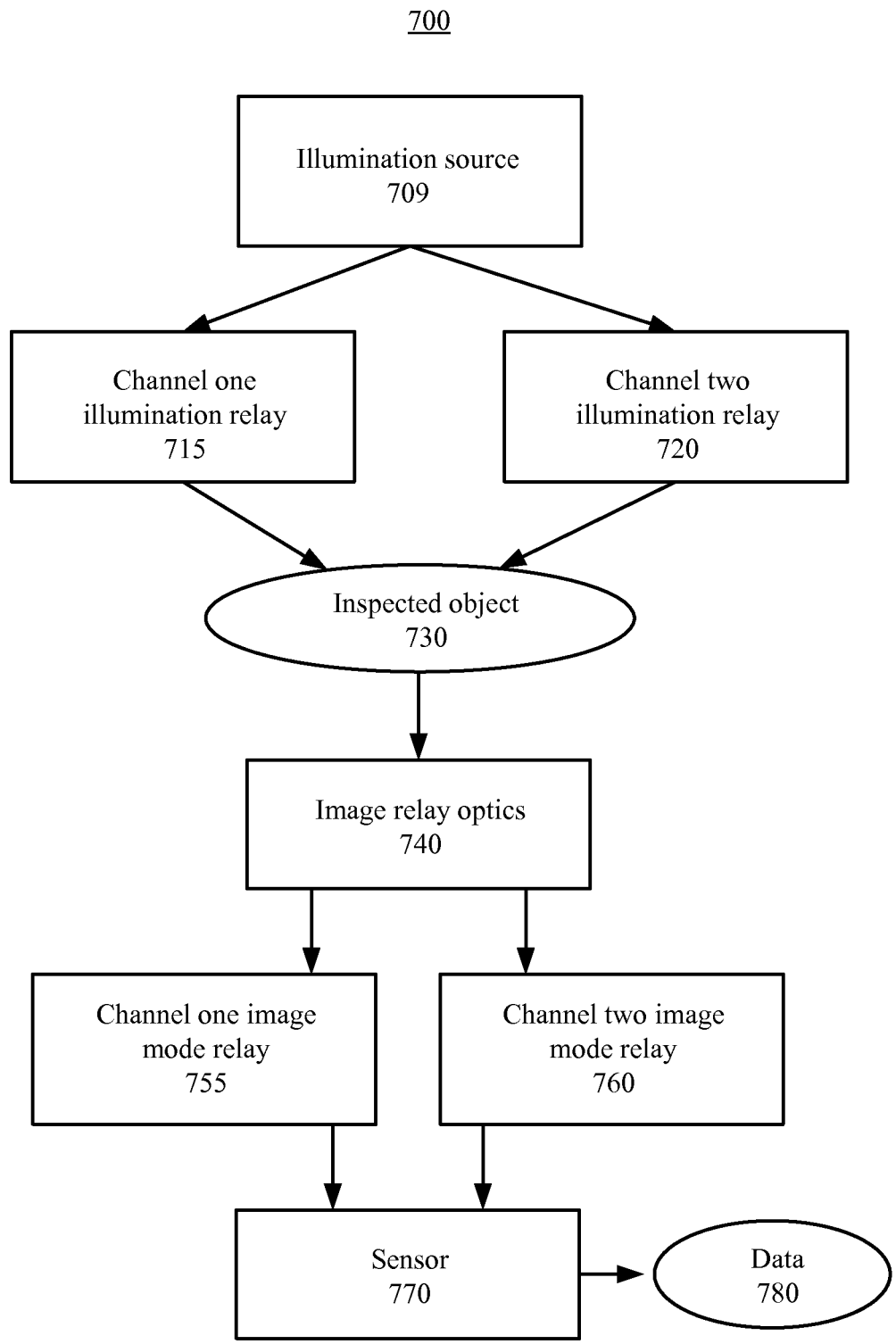
FIG. 7 shows a reticle, photomask, or wafer inspection system that simultaneously detects two channels of image or signal on one sensor.

FIG. 7 shows a reticle, photomask, or wafer inspection system 700 that simultaneously detects two channels of image or signal on one sensor 770. The illumination source 709 incorporates an improved 193 nm laser as described herein. The light source may further comprise a pulse multiplier and/or a coherence reducing scheme. The two channels may comprise reflected and transmitted intensity when an inspected object 730 is transparent (for example a reticle or photomask), or may comprise two different illumination modes, such as angles of incidence, polarization states, wavelength ranges or some combination thereof.

As shown in FIG. 7, illumination relay optics 715 and 720 relay the illumination from source 709 to the inspected object 730. The inspected object 730 may be a reticle, a photomask, a semiconductor wafer or other article to be inspected. Image relay optics 740, 755, and 760 relay the light that is reflected and/or transmitted by the inspected object 730 to the sensor 770. The data corresponding to the detected signals or images for the two channels is shown as data 780 and is transmitted to a computer (not shown) for processing.

Other details of an embodiment of a reticle or photomask inspection system that may be configured to measure transmitted and reflected light from the reticle or photomask are described in U.S. Pat. Nos. 7,352,457 and 7,528,943, which are incorporated by reference herein. Additional details on reticle and photomask inspection systems that may incorporate the improved 193 nm laser are provided by U.S. Pat. Nos. 7,528,943 and 5,563,702, both of which are incorporated by reference herein.

Figure 8:
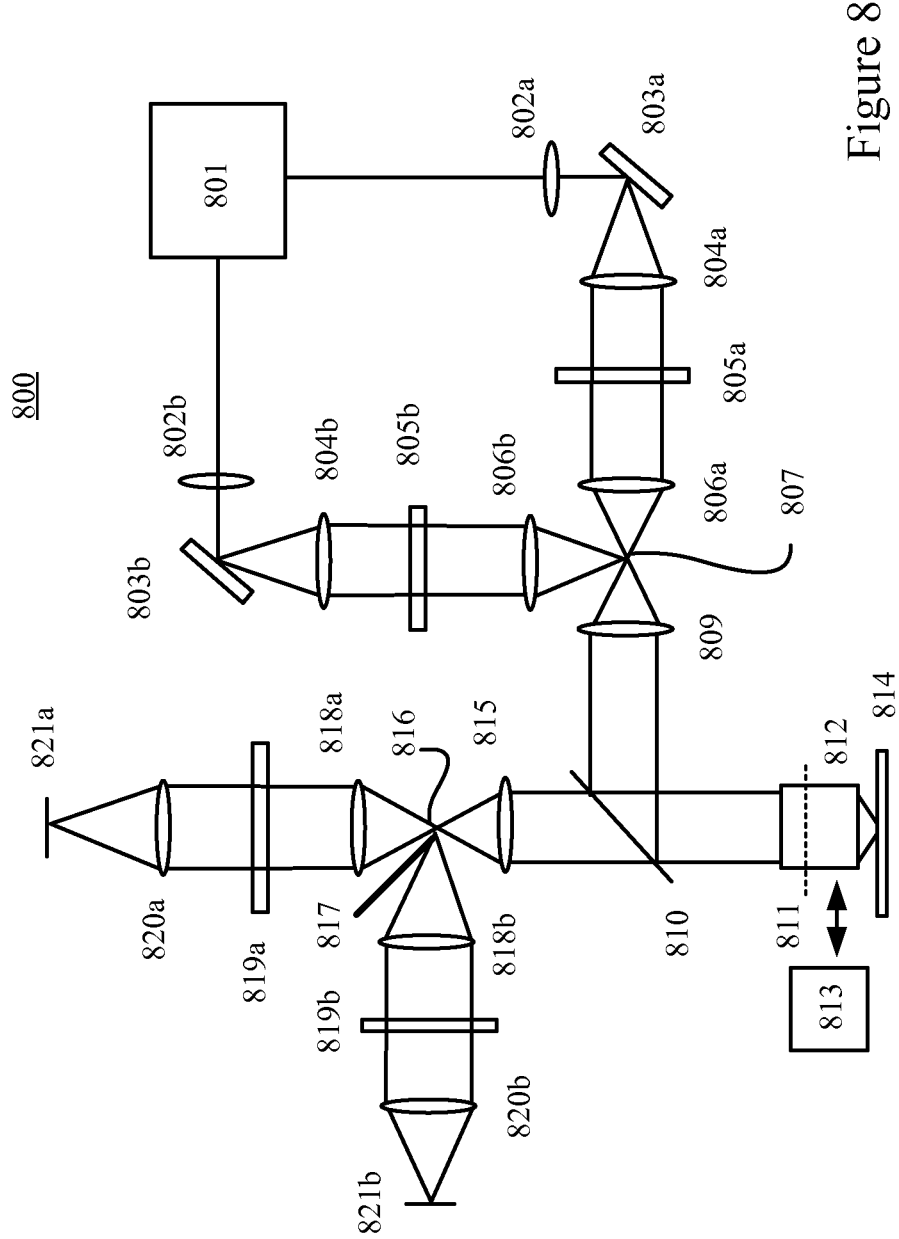
FIG. 8 illustrates an exemplary inspection system including multiple objectives and one of the above-described improved 193 nm lasers.

FIG. 8 illustrates an exemplary inspection system 800 including multiple objectives and one of the above-described improved 193 nm lasers. In system 800, illumination from a laser source 801 is sent to multiple sections of the illumination subsystem. A first section of the illumination subsystem includes elements 802a through 806a. Lens 802a focuses light from laser source 801. Light from lens 802a then reflects from mirror 803a. Mirror 803a is placed at this location for the purposes of illustration, and may be positioned elsewhere. Light from mirror 803a is then collected by lens 804a, which forms illumination pupil plane 805a. An aperture, filter, or other device to modify the light may be placed in pupil plane 805a depending on the requirements of the inspection mode. Light from pupil plane 805a then passes through lens 806a and forms illumination field plane 807.

A second section of the illumination subsystem includes elements 802b through 806b. Lens 802b focuses light from laser source 801. Light from lens 802b then reflects from mirror 803b. Light from mirror 803b is then collected by lens 804b which forms illumination pupil plane 805b. An aperture, filter, or other device to modify the light may be placed in pupil plane 805b depending on the requirements of the inspection mode. Light from pupil plane 805b then passes through lens 806b and forms illumination field plane 807. The light from the second section is then redirected by mirror or reflective surface such that the illumination field light energy at illumination field plane 807 is comprised of the combined illumination sections.

Field plane light is then collected by lens 809 before reflecting off a beamsplitter 810. Lenses 806a and 809 form an image of first illumination pupil plane 805a at objective pupil plane 811. Likewise, lenses 806b and 809 form an image of second illumination pupil plane 805b at objective pupil plane 811. An objective 812 (or alternatively 813) then takes the pupil light and forms an image of illumination field 807 at sample 814. Objective 812 or objective 813 can be positioned in proximity to sample 814. Sample 814 can move on a stage (not shown), which positions the sample in the desired location. Light reflected and scattered from the sample 814 is collected by the high NA catadioptric objective 812 or objective 813. After forming a reflected light pupil at objective pupil plane 811, light energy passes through beamsplitter 810 and lens 815 before forming an internal field 816 in the imaging subsystem. This internal imaging field is an image of sample 814 and correspondingly illumination field 807. This field may be spatially separated into multiple fields corresponding to the illumination fields. Each of these fields can support a separate imaging mode. For example, one imaging mode may be a bright-field imaging mode, while another may be a dark-field imaging mode.

One of these fields can be redirected using mirror 817. The redirected light then passes through lens 818b before forming another imaging pupil 819b. This imaging pupil is an image of pupil 811 and correspondingly illumination pupil 805b. An aperture, filter, or other device to modify the light may be placed in pupil plane 819b depending on the requirements of the inspection mode. Light from pupil plane 819b then passes through lens 820b and forms an image on sensor 821b. In a similar manner, light passing by mirror or reflective surface 817 is collected by lens 818a and forms imaging pupil 819a. Light from imaging pupil 819a is then collected by lens 820a before forming an image on detector 821a. Light imaged on detector 821a can be used for a different imaging mode from the light imaged on sensor 821b.

The illumination subsystem employed in system 800 is composed of laser source 801, collection optics 802-804, beam shaping components placed in proximity to a pupil plane 805, and relay optics 806 and 809. An internal field plane 807 is located between lenses 806 and 809. In one preferred configuration, laser source 801 can include one of the above-described improved 193 nm lasers.

With respect to laser source 801, while illustrated as a single uniform block having two points or angles of transmission, in reality this represents a laser source able to provide two channels of illumination, for example a first channel of light energy such as laser light energy at a first frequency (e.g. a deep UV wavelength near 193 nm) which passes through elements 802a-806a, and a second channel of light energy such as laser light energy at a second frequency (e.g. a different harmonic, such as the $4^{th}$ harmonic, from the same laser, or a light from a different laser) which passes through elements 802b-806b.

While light energy from laser source 801 is shown to be emitted 90 degrees apart, and the elements 802a-806a and 802b-806b are oriented at 90 degree angles, in reality light may be emitted at various orientations, not necessarily in two dimensions, and the components may be oriented differently than as shown. FIG. 8 is therefore simply a representation of the components employed and the angles or distances shown are not to scale nor specifically required for the design.

Elements placed in proximity to pupil plane 805a/805b may be employed in the current system using the concept of aperture shaping. Using this design, uniform illumination or near uniform illumination may be realized, as well as individual point illumination, ring illumination, quadrapole illumination, or other desirable patterns.

Various implementations for the objectives may be employed in a general imaging subsystem. A single fixed objective may be used. The single objective may support all the desired imaging and inspection modes. Such a design is achievable if the imaging system supports a relatively large field size and relatively high numerical aperture. Numerical aperture can be reduced to a desired value by using internal apertures placed at the pupil planes 805a, 805b, 819a, and 819b.

Multiple objectives may also be used as shown in FIG. 8. For example, although two objectives 812 and 813 are shown, any number is possible. Each objective in such a design may be optimized for each wavelength produced by laser source 801. These objectives 812 and 813 can either have fixed positions or be moved into position in proximity to the sample 814. To move multiple objectives in proximity to the sample, rotary turrets may be used as are common on standard microscopes. Other designs for moving objectives in proximity of a sample are available, including but not limited to translating the objectives laterally on a stage, and translating the objectives on an arc using a goniometer. In addition, any combination of fixed objectives and multiple objectives on a turret can be achieved in accordance with the present system.

The maximum numerical apertures of this configuration may approach or exceed 0.97, but may in certain instances be smaller. The wide range of illumination and collection angles possible with this high NA catadioptric imaging system, combined with its large field size allows the system to simultaneously support multiple inspection modes. As may be appreciated from the previous paragraphs, multiple imaging modes can be implemented using a single optical system or machine in connection with the illumination device. The high NA disclosed for illumination and collection permits the implementation of imaging modes using the same optical system, thereby allowing optimization of imaging for different types of defects or samples.

The imaging subsystem also includes intermediate image forming optics 815. The purpose of the image forming optics 815 is to form an internal image 816 of sample 814. At this internal image 816, a mirror 817 can be placed to redirect light corresponding to one of the inspection modes. It is possible to redirect the light at this location because the light for the imaging modes are spatially separate. The image forming optics 818 (818a and 818b) and 820 (820a and 820b) can be implemented in several different forms including a varifocal zoom, multiple afocal tube lenses with focusing optics, or multiple image forming mag tubes. U.S. Published Application 2009/0180176, which published on Jul. 16, 2009 and is incorporated by reference herein, describes additional details regarding system 800.

Figure 9:
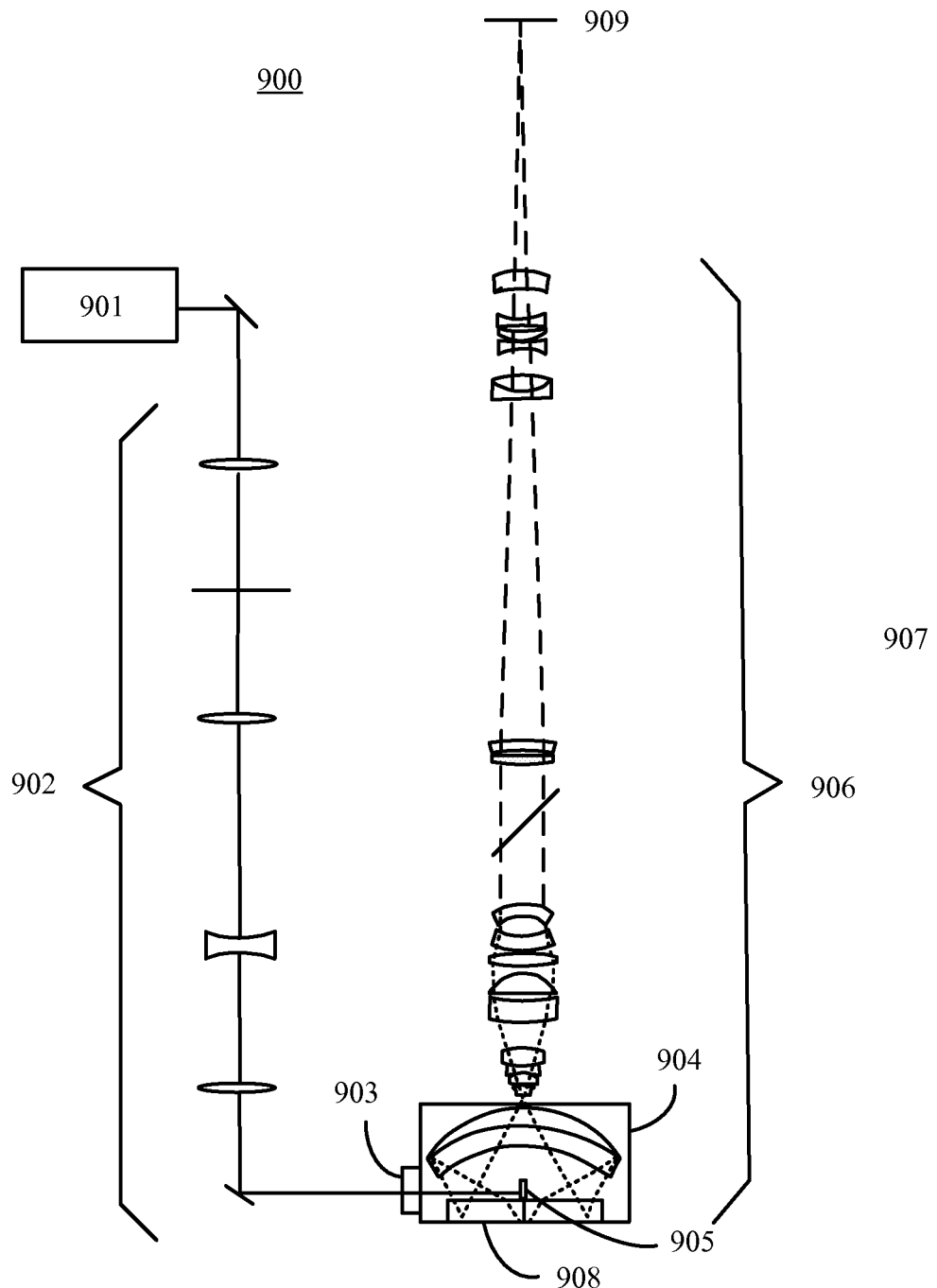
FIG. 9 illustrates the addition of a normal incidence laser dark-field illumination to a catadioptric imaging system.

FIG. 9 illustrates the addition of a normal incidence laser dark-field illumination to a catadioptric imaging system 900. The dark-field illumination includes a laser 901, adaptation optics 902 to control the illumination beam size and profile on the surface being inspected, an aperture and window 903 in a mechanical housing 904, and a prism 905 to redirect the laser along the optical axis at normal incidence to the surface of a sample 908. Prism 905 also directs the specular reflection from surface features of sample 908 and reflections from the optical surfaces of an objective 906 along the optical path to an image plane 909. Lenses for objective 906 can be provided in the general form of a catadioptric objective, a focusing lens group, and a zooming tube lens section. In a preferred embodiment, laser 901 can be implemented by the one of the above-described improved 193 nm lasers. Published US Patent Application 2007/0002465, which published on Jan. 4, 2007 and is incorporated by reference herein, describes system 900 in further detail.

Figure 10A:
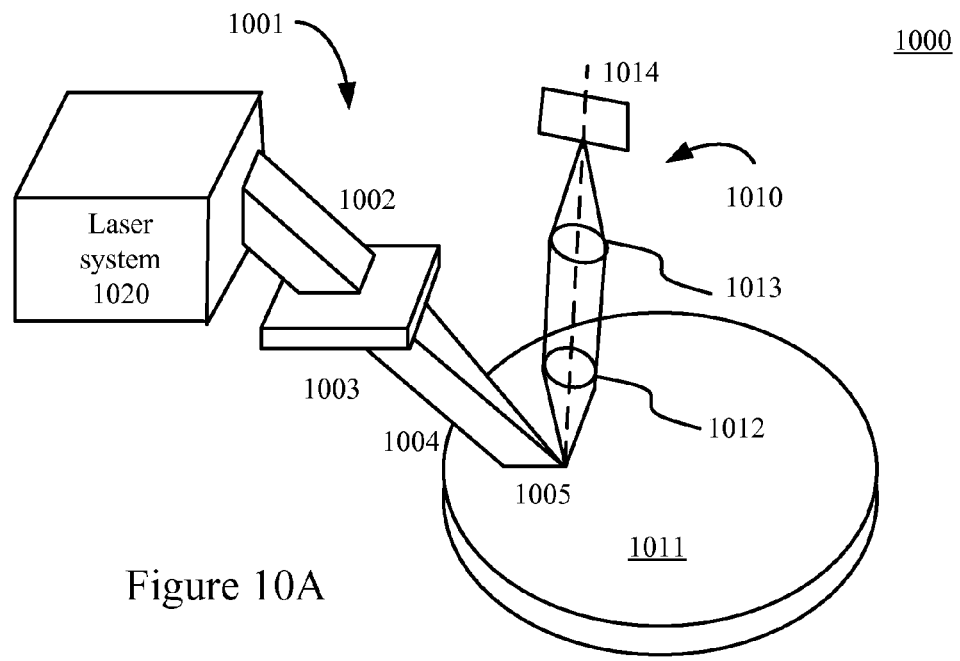
FIG. 10A illustrates a surface inspection apparatus that includes an illumination system and a collection system for inspecting areas of a surface.

FIG. 10A illustrates a surface inspection apparatus 1000 that includes illumination system 1001 and collection system 1010 for inspecting areas of surface 1011. As shown in FIG. 10A, a laser system 1020 directs a light beam 1002 through a lens 1003. In a preferred embodiment, laser system 1020 includes one of the above-described improved 193 nm lasers, an annealed crystal, and a housing to maintain the annealed condition of the crystal during standard operation by protecting it from moisture or other environmental contaminants. First beam shaping optics can be configured to receive a beam from the laser and focus the beam to an elliptical cross section at a beam waist in or proximate to the crystal.

Lens 1003 is oriented so that its principal plane is substantially parallel to a sample surface 1011 and, as a result, illumination line 1005 is formed on surface 1011 in the focal plane of lens 1003. In addition, light beam 1002 and focused beam 1004 are directed at a non-orthogonal angle of incidence to surface 1011. In particular, light beam 1002 and focused beam 1004 may be directed at an angle between about 1 degree and about 85 degrees from a normal direction to surface 1011. In this manner, illumination line 1005 is substantially in the plane of incidence of focused beam 1004.

Collection system 1010 includes lens 1012 for collecting light scattered from illumination line 1005 and lens 1013 for focusing the light coming out of lens 1012 onto a device, such as charge coupled device (CCD) 1014, comprising an array of light sensitive detectors. In one embodiment, CCD 1014 may include a linear array of detectors. In such cases, the linear array of detectors within CCD 1014 can be oriented parallel to illumination line 1015. In one embodiment, multiple collection systems can be included, wherein each of the collection systems includes similar components, but differ in orientation.

Figure 10B:
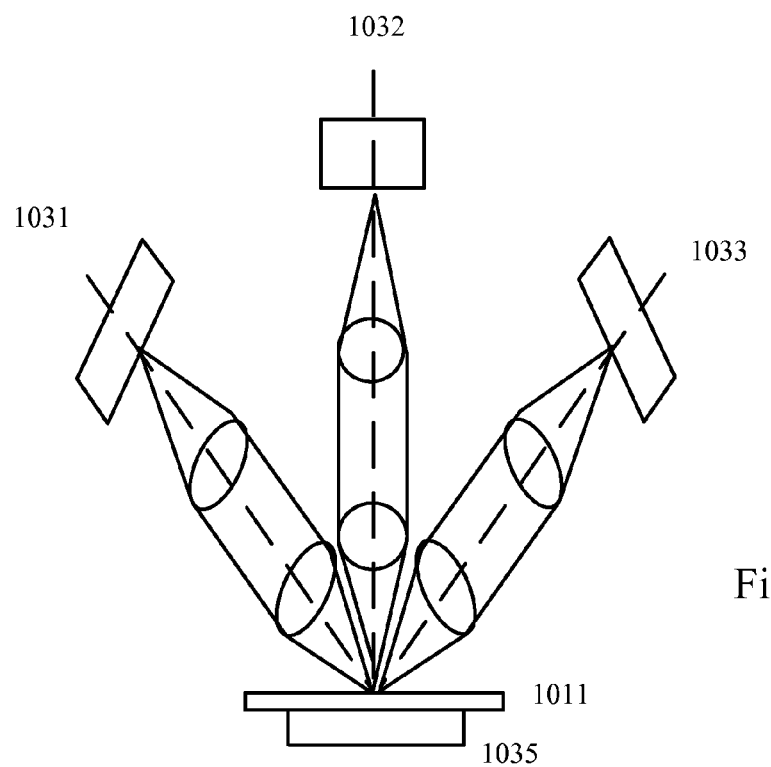
FIG. 10B illustrates an exemplary array of collection systems for a surface inspection apparatus.

For example, FIG. 10B illustrates an exemplary array of collection systems 1031, 1032, and 1033 for a surface inspection apparatus (wherein its illumination system, e.g. similar to that of illumination system 1001, is not shown for simplicity). First optics in collection system 1031 collect light scattered in a first direction from the surface of sample 1011. Second optics in collection system 1032 collect light scattered in a second direction from the surface of sample 1011. Third optics in collection system 1033 collect light scattered in a third direction from the surface of sample 1011. Note that the first, second, and third paths are at different angles of incidence to said surface of sample 1011. A platform 1035 supporting sample 1011 can be used to cause relative motion between the optics and sample 1011 so that the whole surface of sample 1011 can be scanned. U.S. Pat. No. 7,525,649, which issued on Apr. 28, 2009 and is incorporated by reference herein, describes surface inspection apparatus 1000 and other multiple collection systems in further detail.

Figure 11:
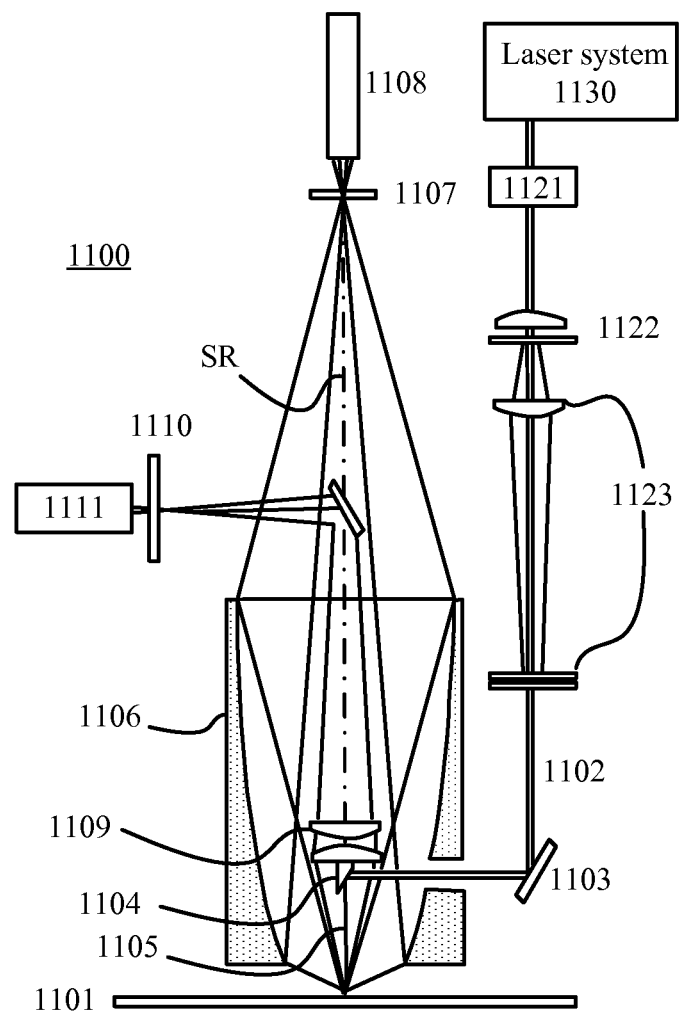
FIG. 11 illustrates a surface inspection system that can be used for inspecting anomalies on a surface.

FIG. 11 illustrates a surface inspection system 1100 that can be used for inspecting anomalies on a surface 1101. In this embodiment, surface 1101 can be illuminated by a substantially stationary illumination device portion of a laser system 1130 comprising one of the above-described improved 193 nm lasers. The output of laser system 1130 can be consecutively passed through polarizing optics 1121, a beam expander and aperture 1122, and beam-forming optics 1123 to expand and focus the beam.

The focused laser beam 1102 is then reflected by a beam folding component 1103 and a beam deflector 1104 to direct the beam 1105 towards surface 1101 for illuminating the surface. In the preferred embodiment, beam 1105 is substantially normal or perpendicular to surface 1101, although in other embodiments beam 1105 may be at an oblique angle to surface 1101.

In one embodiment, beam 1105 is substantially perpendicular or normal to surface 1101 and beam deflector 1104 reflects the specular reflection of the beam from surface 1101 towards beam turning component 1103, thereby acting as a shield to prevent the specular reflection from reaching the detectors. The direction of the specular reflection is along line SR, which is normal to the surface 1101 of the sample. In one embodiment where beam 1105 is normal to surface 1101, this line SR coincides with the direction of illuminating beam 1105, where this common reference line or direction is referred to herein as the axis of inspection system 1100. Where beam 1105 is at an oblique angle to surface 1101, the direction of specular reflection SR would not coincide with the incoming direction of beam 1105; in such instance, the line SR indicating the direction of the surface normal is referred to as the principal axis of the collection portion of inspection system 1100.

Light scattered by small particles are collected by mirror 1106 and directed towards aperture 1107 and detector 1108. Light scattered by large particles are collected by lenses 1109 and directed towards aperture 1110 and detector 1111. Note that some large particles will scatter light that is also collected and directed to detector 1107, and similarly some small particles will scatter light that is also collected and directed to detector 1111, but such light is of relatively low intensity compared to the intensity of scattered light the respective detector is designed to detect. In one embodiment, detector 1111 can include an array of light sensitive elements, wherein each light sensitive element of the array of light sensitive elements is configured to detect a corresponding portion of a magnified image of the illumination line. In one embodiment, inspection system can be configured for use in detecting defects on unpatterned wafers. U.S. Pat. No. 6,271,916, which issued to Marx et al. on Aug. 7, 2001 and is incorporated by reference herein, describes inspection system 1100 in further detail.

Figure 12:
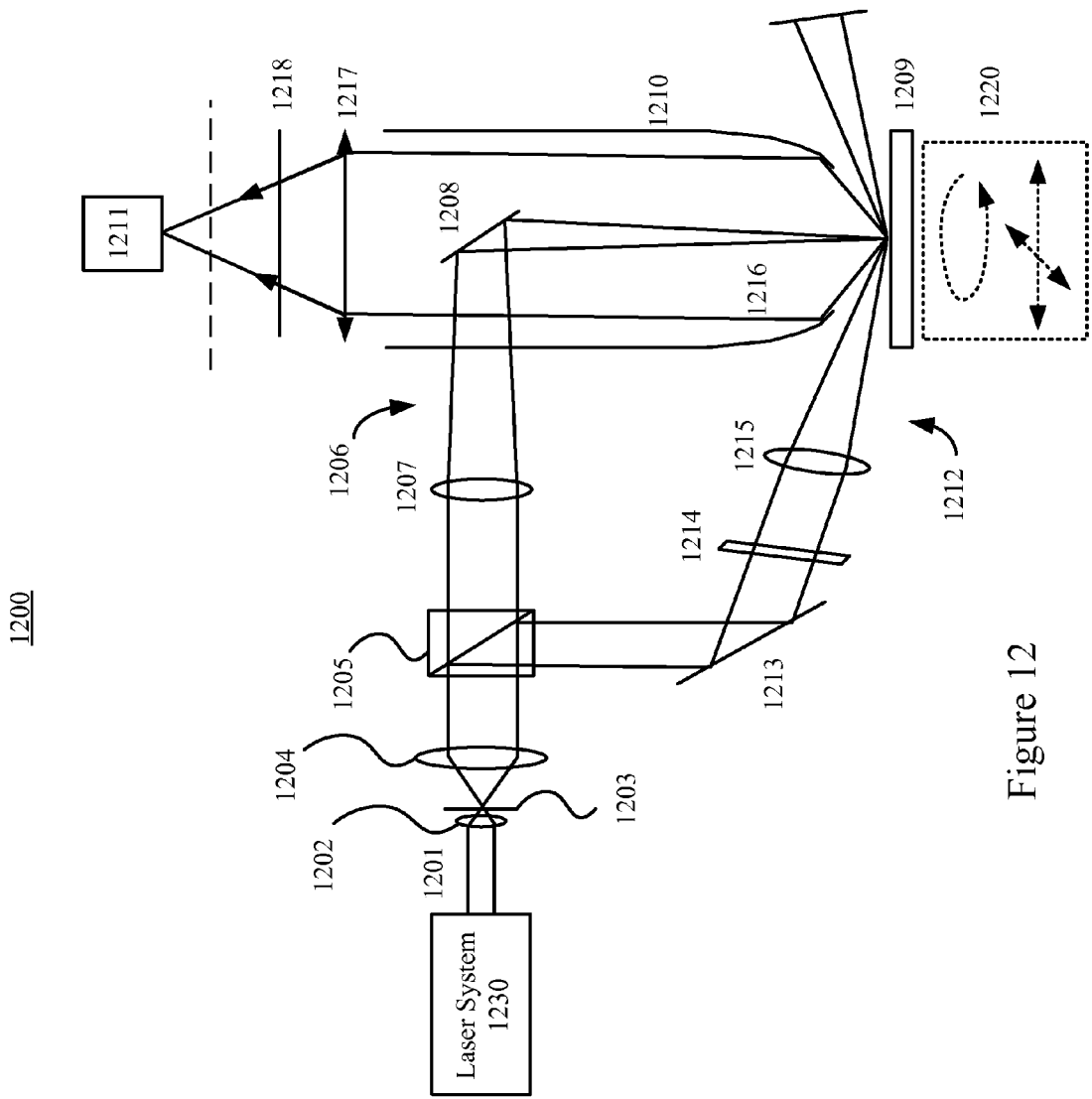
FIG. 12 illustrates an inspection system configured to implement anomaly detection using both normal and oblique illumination beams.

FIG. 12 illustrates an inspection system 1200 configured to implement anomaly detection using both normal and oblique illumination beams. In this configuration, a laser system 1230, which includes one of the above-described improved 193 nm lasers, can provide a laser beam 1201. A lens 1202 focuses the beam 1201 through a spatial filter 1203 and lens 1204 collimates the beam and conveys it to a polarizing beam splitter 1205. Beam splitter 1205 passes a first polarized component to the normal illumination channel and a second polarized component to the oblique illumination channel, where the first and second components are orthogonal. In the normal illumination channel 1206, the first polarized component is focused by optics 1207 and reflected by mirror 1208 towards a surface of a sample 1209. The radiation scattered by sample 1209 is collected and focused by a paraboloidal mirror 1210 to a detector or photomultiplier tube 1211.

In the oblique illumination channel 1212, the second polarized component is reflected by beam splitter 1205 to a mirror 1213 which reflects such beam through a half-wave plate 1214 and focused by optics 1215 to sample 1209. Radiation originating from the oblique illumination beam in the oblique channel 1212 and scattered by sample 1209 is collected by paraboloidal mirror 1210 and focused to photomultiplier tube 1211. Detector or photomultiplier tube 1211 has a pinhole entrance. The pinhole and the illuminated spot (from the normal and oblique illumination channels on surface 1209) are preferably at the foci of the paraboloidal mirror 1210.

The paraboloidal mirror 1210 collimates the scattered radiation from sample 1209 into a collimated beam 1216. Collimated beam 1216 is then focused by an objective 1217 and through an analyzer 1218 to the photomultiplier tube 1211. Note that curved mirrored surfaces having shapes other than paraboloidal shapes may also be used. An instrument 1220 can provide relative motion between the beams and sample 1209 so that spots are scanned across the surface of sample 1209. U.S. Pat. No. 6,201,601, which issued to Vaez-Iravani et al. on Mar. 13, 2001 and is incorporated by reference herein, describes inspection system 1200 in further detail.

Figure 13:
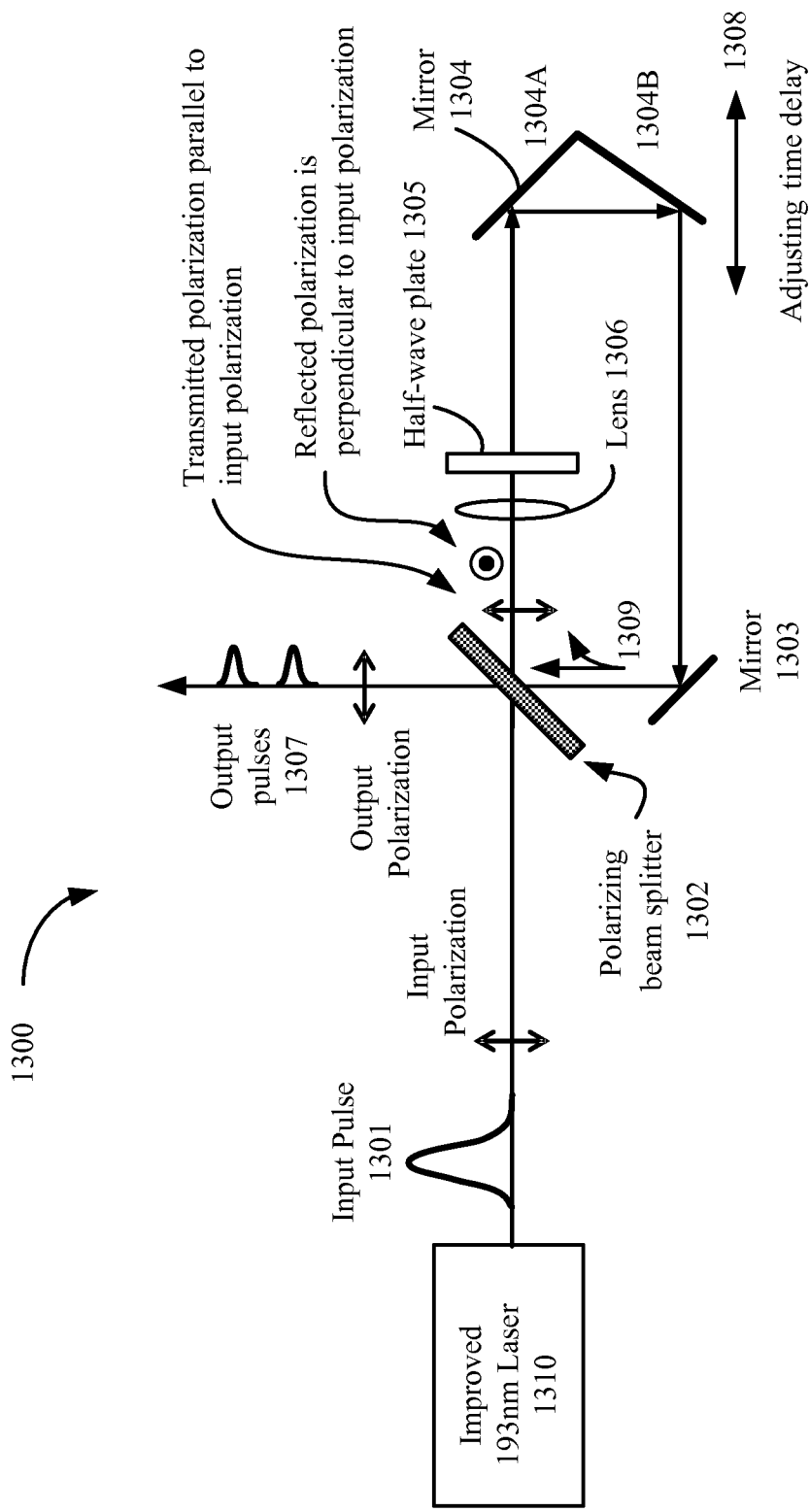
FIG. 13 illustrates an exemplary pulse multiplier for use with the above-described improved 193 nm laser in an inspection or metrology system.

FIG. 13 illustrates an exemplary pulse multiplier 1300 for use with the above-described improved 193 nm laser in an inspection or metrology system. Pulse multiplier 1300 is configured to generate pulse trains from each input pulse 1301 from improved 193 nm laser 1310. Input pulse 1301 impinges on a polarizing beam splitter 1302, which because of the polarization of input pulse 1301, transmits all of its light to a lens 1306. Thus, the transmitted polarization is parallel to the input polarization of input pulse 1301. Lens 1306 focuses and directs the light of input pulse 1301 to a half-wave plate 1305. In general, a wave plate can shift the phases between perpendicular polarization components of a light wave. For example, a half-wave plate receiving linearly polarized light can generate two waves, one wave parallel to the optical axis and another wave perpendicular to the optical axis. In half-wave plate 1305, the parallel wave can propagate slightly slower than the perpendicular wave. Half-wave plate 105 is fabricated such that for light exiting, one wave is exactly half of a wavelength delayed (180 degrees) relative to the other wave.

Thus, half-wave plate 1305 can generate pulse trains from each input pulse 1301. The normalized amplitudes of the pulse trains are: $\cos 2\theta$ (wherein $\theta$ is the angle of half-wave plate 1305), $\sin^2 2\theta$, $\sin^2 2\theta \cos 2\theta$, $\sin^2 2\theta \cos^2 2\theta$, $\sin^2 2\theta \cos^3 2\theta$, $\sin^2 2\theta \cos^4 2\theta$, $\sin^2 2\theta \cos^5 2\theta$, etc. Notably, the total energy of the pulse trains from a laser pulse can be substantially conserved traversing half-wave plate 1305.

The sum of the energy from the odd terms generated by half-wave plate 1305 is equal to:

$$(\cos 2\theta)^2 + (\sin^2 2\theta \cos 2\theta)^2 + (\sin^2 2\theta \cos^3 2\theta)^2 +$$
$$(\sin^2 2\theta \cos^5 2\theta)^2 + (\sin^2 2\theta \cos^7 2\theta)2 + (\sin^2 2\theta \cos^9 2\theta)^2 + \ldots =$$
$$\cos^2 2\theta + \sin^4 2\theta (\cos^2 2\theta + \cos^6 2\theta + \cos^{10} 2\theta + \ldots) = 2\cos^2 2\theta / (1 + \cos^2 2\theta)$$

In contrast, the sum of the energy from the even terms generated by half-wave plate 1305 is equal to:

$$(\sin^2 2\theta)^2 + (\sin^2 2\theta \cos^2 2\theta)^2 + (\sin^2 2\theta \cos^4 2\theta)^2 +$$
$$(\sin^2 2\theta \cos^6 2\theta)^2 + (\sin^2 2\theta \cos^8 2\theta)^2 + (\sin^2 2\theta \cos^{10} 2\theta)^2 + \ldots =$$
$$\sin^4 2\theta (1 + \cos^4 2\theta + \cos^8 2\theta + \cos^{12} 2\theta + \ldots) = \sin^2 2\theta / (1 + \cos^2 2\theta)$$

In accordance with one aspect of pulse multiplier 1300, the angle $\theta$ of half-wave plate 1305 can be determined (as shown below) to provide that the odd term sum is equal to the even term sum.

$2\cos^2 2\theta = \sin^2 2\theta$ $\cos^2 2\theta = 1/3$ $\sin^2 2\theta = 2/3$ $\theta = 27.4$ degrees The light exiting half-wave plate 1305 is reflected by mirrors 1304 and 1303 back to polarizing beam splitter 1302. Thus, polarizing beam splitter 1302, lens 1306, half-wave plate 1305, and mirrors 1304 and 1303 form a ring cavity configuration. The light impinging on polarizing beam splitter 1302 after traversing the ring cavity has two polarizations as generated by half-wave plate 1305. Therefore, polarizing beam splitter 1302 transmits some light and reflects other light, as indicated by arrows 1309. Specifically, polarizing beam splitter 1302 transmits the light from mirror 1303 having the same polarization as input pulse 1301. This transmitted light exits pulse multiplier 1300 as output pulses 1307. The reflected light, which has a polarization perpendicular to that of input pulse 1301, is re-introduced into the ring cavity (pulses not shown for simplicity).

Notably, these re-introduced pulses can traverse the ring in the manner described above with further partial polarization switching by half-wave plate 1305 and then light splitting by polarizing beam splitter 1302. Thus, in general, the above-described ring cavity is configured to allow some light to exit and the rest of the light (with some minimal losses) to continue around the ring. During each traversal of the ring (and without the introduction of additional input pulses), the energy of the total light decreases due to the light exiting the ring as output pulses 1307.

Periodically, a new input pulse 1301 is provided by laser 1310 to pulse multiplier 1300. In one embodiment, the laser may generate approximately 0.1 nanosecond (ns) laser pulses at a repetition rate of approximately 125 MHz, and the cavity may double the repetition rate. Note that the size of the ring, and thus the time delay of the ring, can be adjusted by moving mirror 1304 along the axis indicated by arrows 1308.

The ring cavity length may be slightly greater than, or slightly less than, the nominal length calculated directly from the pulse interval divided by the multiplication factor. This results in the pulses not arriving at exactly the same time as the polarized beam splitter and slightly broadens the output pulse. For example, when the input pulse repetition rate is 125 MHz, the cavity delay would nominally be 4 ns for a frequency multiplication by 2. In one embodiment, a cavity length corresponding to 4.05 ns can be used so that the multiply reflected pulses do not arrive at exactly the same time as an incoming pulse. Moreover, the 4.05 ns cavity length for the 125 MHz input pulse repetition rate can also advantageously broaden the pulse and reduce pulse height. Other pulse multipliers having different input pulse rates can have different cavity delays.

Notably, polarizing beam splitter 1302 and half-wave plate 1305 working in combination generate even and odd pulses, which diminish for each round traversed inside the ring. These even and odd pulses can be characterized as providing energy envelopes, wherein an energy envelope consists of an even pulse train (i.e. a plurality of even pulses) or an odd pulse train (i.e. a plurality of odd pulses). In accordance with one aspect of pulse multiplier 1300, these energy envelopes are substantially equal.

More details of pulse multiplication can be found in co-pending U.S. patent application Ser. No. 13/487,075, entitled "Semiconductor Inspection And Metrology System Using Laser Pulse Multiplier" and filed on Jun. 1, 2012, which is incorporated by reference herein. Note that the above pulse multiplier is just one example that may be used with the improved 193 nm laser. Combining this improved laser with other pulse multipliers is within the scope of this invention. For example, the improved 193 nm laser described herein may also be used with any of the laser pulse multipliers described in U.S. patent application Ser. No. 13/711,593, entitled "Semiconductor Inspection and Metrology System Using Laser Pulse Multiplier", filed by Chuang et al. on Dec. 11, 2012, and incorporated by reference herein.

Figure 14:
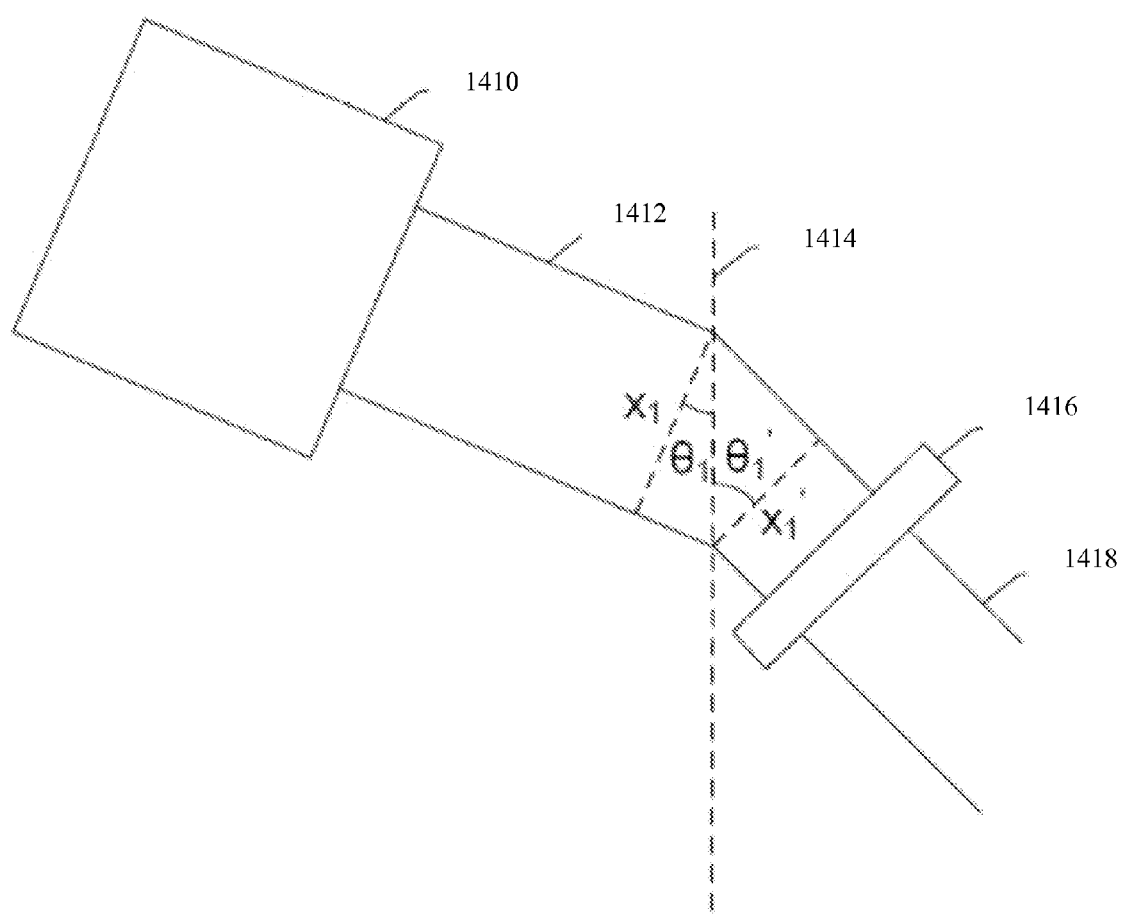
FIG. 14 illustrates a coherence reducing subsystem for use with the above-described improved 193 nm laser in an inspection or metrology system.

FIG. 14 illustrates aspects of a pulse-shaping or coherence reducing device used in conjunction with a pulsed laser, suitable for incorporation into an inspection or metrology system in accordance with embodiments of the present invention. A light source 1410 comprises an improved 193 nm laser as described herein. The light source 1410 generates a light beam 1412 comprising a series of pulses. One aspect of this embodiment is to make use of the finite spectral range of the laser in order to perform a substantially quick temporal modulation of a light beam 1412, which can be changed on the required tenth picosecond time intervals (a tenth picoseconds time interval is equivalent to a few nm in spectral width), and transform the temporal modulation to spatial modulation.

The use of a dispersive element and an electro-optic modulator is provided for speckle reduction and/or pulse shaping.

For example, the illumination subsystem includes a dispersive element positioned in the path of the coherent pulses of light. As shown in FIG. 14, the dispersive element can be positioned at a plane 1414 arranged at angle $\theta_1$ to the cross-section of the coherent pulses of light. As shown in FIG. 14, the pulses of light exit the dispersive element at angle $\theta_1'$ and with cross-sectional dimension $x_1'$. In one embodiment, the dispersive element is a prism. In another embodiment, the dispersive element is a diffraction grating. The dispersive element is configured to reduce coherence of the pulses of light by mixing spatial and temporal characteristics of light distribution in the pulses of light. In particular, a dispersive element such as a prism or diffraction grating provides some mixing between spatial and temporal characteristics of the light distribution in the pulses of light. The dispersive element may include any suitable prism or diffraction grating, which may vary depending on the optical characteristics of the illumination subsystem and the metrology or inspection system.

The illumination subsystem further includes an electro-optic modulator positioned in the path of the pulses of light exiting the dispersive element. For example, as shown in FIG. 14, the illumination subsystem may include an electro-optic modulator 1416 positioned in the path of the pulses of light exiting the dispersive element. The electro-optic modulator 1416 is configured to reduce the coherence of the pulses of light by temporally modulating the light distribution in the pulses of light. In particular, the electro-optic modulator 1416 provides an arbitrary temporal modulation of the light distribution. Therefore, the dispersive element and the electro-optic modulator 1416 have a combined effect on the pulses of light generated by the light source. In particular, the combination of the dispersive element with the electro-optic modulator 1416 creates an arbitrary temporal modulation and transforms the temporal modulation to an arbitrary spatial modulation of the output beam 1418.

In one embodiment, the electro-optic modulator 1416 is configured to change the temporal modulation of the light distribution in the pulses of light at tenth picosecond time intervals. In another embodiment, the electro-optic modulator 1416 is configured to provide about $10^3$ aperiodic samples on each period thereby providing a de-coherence time of about $10^{-13}$ seconds.

Further details of the pulse-shaping, coherence, and speckle reducing apparatus and methods are disclosed in co-pending U.S. Published Patent Application 2011/0279819, published on Nov. 17, 2011, and U.S. Published Patent Application 2011/0228263, published on Sep. 22, 2011. Both of these applications are incorporated by reference herein.

The various embodiments of the structures and methods described herein are illustrative only of the principles of the invention and are not intended to limit the scope of the invention to the particular embodiments described. For example, non-linear crystals other than CLBO, LBO, or BBO or periodically-poled materials can be used for some of the frequency conversion and mixing stages.

The invention claimed is:

1. A laser for generating an output wavelength of approximately 193.4 nm, the laser comprising:
   a fundamental laser;
   a first frequency doubling module, coupled to the fundamental laser, for generating a second harmonic;
   a second frequency doubling module, coupled to the first frequency doubling module, for generating a fourth harmonic;
   an optical parametric generator, coupled to one of the first frequency doubling module and the fundamental laser, for generating a down-converted signal; and
   a frequency mixing module, coupled to the optical parametric generator and the second frequency doubling module, for generating a laser output of a frequency equal to a sum of the fourth harmonic and twice a frequency of the down-converted signal,
   wherein the frequency mixing module comprises two non-linear crystals, a first non-linear crystal configured to generate a frequency equal to a sum of the fourth harmonic and a frequency of the down-converted signal by type-I conversion, and a second non-linear crystal configured to generate the frequency equal to the sum of the fourth harmonic and the twice the frequency of the down-converted signal by type-II conversion, and
   wherein the fundamental laser generates a fundamental frequency of approximately 1064.3 nm, approximately 1053 nm, approximately 1047 nm, or approximately 1030 nm.

2. The laser of claim 1, wherein the optical parametric generator includes a periodically poled non-linear optical crystal.

3. The laser of claim 2, wherein the periodically poled non-linear optical crystal is one of lithium niobate, magnesium-oxide doped lithium niobate, stoichiometric lithium tantalate, magnesium-oxide doped stoichiometric lithium tantalate, and potassium titanyl phosphate (KTP).

4. The laser of claim 1, wherein the down-converted signal has a signal wavelength of approximately 1380 nm to 1612 nm.

5. The laser of claim 4, wherein the down-converted signal has a signal wavelength of approximately 1416 nm.

6. The laser of claim 1, wherein the laser is one of a continuous-wave laser, a Q-switched laser, a mode-locked laser, or a quasi-continuous-wave laser.

7. The laser of claim 1, wherein the optical parametric generator includes an optical parametric amplifier or an optical parametric oscillator.

8. The laser of claim 1, wherein the fundamental laser includes a laser diode or a fiber laser.

9. The laser of claim 1, wherein the fundamental laser includes a cesium lithium borate (CLBO) crystal.

10. The laser of claim 1, wherein the frequency mixing module includes a cesium lithium borate (CLBO) crystal, a beta barium borate (BBO) crystal, or a lithium triborate (LBO) crystal.

11. The laser of claim 1, wherein the frequency mixing module comprises a hydrogen-annealed non-linear crystal.

12. An inspection system comprising:
   a laser for generating an output wavelength of approximately 193.4 nm, the laser comprising:
      a fundamental laser;
      an optical parametric generator, coupled to the fundamental laser, for generating a down-converted signal;
      a fourth harmonic generator, coupled to the optical parametric generator or to the fundamental laser, for generating a fourth harmonic; and
      a frequency mixing module, coupled to the optical parametric generator and the fourth harmonic generator, for generating a laser output at a frequency equal to a sum of the fourth harmonic and twice a frequency of the down-converted signal,
      wherein the frequency mixing module comprises two non-linear crystals configured so that one non-linear crystal performs type-I frequency summation and another nonlinear crystal performs type-II frequency summation, and wherein the inspection system further comprises a detector and optics configured to simultaneously collect reflection and transmission images using the detector.

13. The inspection system of claim 12, wherein the inspection system is a dark-field inspection system.

14. The inspection system of claim 12, further comprising at least one acousto-optic modulator or electro-optic modulator to reduce coherence of illumination.

15. The inspection system of claim 12, further comprising a pulse rate multiplier to increase a pulse repetition rate.

16. The inspection system of claim 12, further comprising components for simultaneously collecting reflection and transmission images using same detectors.

17. The inspection system of claim 12, further comprising components for forming an illuminated line on a target being inspected.

18. The inspection system of claim 12, further comprising components for forming multiple, simultaneously-illuminated spots on a target.

19. The inspection system of claim 12, wherein the fundamental laser generates a fundamental frequency of approximately 1064.3 nm, approximately 1053 nm, approximately 1047 nm, or approximately 1030 nm.

20. A laser for generating an output wavelength of approximately 193.4 nm, the laser comprising:
a fundamental laser;
a frequency doubling module, coupled to the fundamental laser, for generating a second harmonic;
a frequency combiner, coupled to the frequency doubling module, for generating a third harmonic;
an optical parametric generator, coupled to one of the frequency doubling module and the frequency combiner, for generating a down-converted signal; and
a frequency mixing module, coupled to the optical parametric generator and the frequency combiner, for generating a laser output of a frequency equal to a sum of the third harmonic and twice a frequency of the down-converted signal,
wherein the fundamental laser generates a fundamental frequency of approximately 1064.3 nm, approximately 1053 nm, approximately 1047 nm, or approximately 1030 nm.

* * * * *